United States Patent [19]

Richardson et al.

[11] Patent Number: 5,047,548
[45] Date of Patent: Sep. 10, 1991

[54] 3-ARYL-3-HYDROXY-4-(1H-1,2,4-TRIAZOL-1-YL)BUTYRAMIDE AND DERIVATIVES AS ANTIFUNGAL AGENTS

[75] Inventors: Kenneth Richardson, Birchington; Geoffrey E. Gymer, Canterbury, both of England

[73] Assignee: Pfizer Inc., New York, N.Y.

[21] Appl. No.: 149,031

[22] Filed: Jan. 27, 1988

Related U.S. Application Data

[63] Continuation-in-part of Ser. No. 808,390, Nov. 29, 1985, abandoned, which is a continuation of Ser. No. 535,973, Sep. 26, 1983, abandoned.

[30] Foreign Application Priority Data

Sep. 30, 1982 [GB] United Kingdom ............... 8227978
Feb. 2, 1983 [GB] United Kingdom ............... 8302888

[51] Int. Cl.$^5$ .............................................. C07D 249/08
[52] U.S. Cl. .................................................. 548/267.6
[58] Field of Search ........................... 548/262, 267.6

[56] References Cited

U.S. PATENT DOCUMENTS

| 4,079,143 | 3/1978 | Balasubramanyan et al. | 514/383 |
|---|---|---|---|
| 4,331,674 | 5/1982 | Kramer et al. | 544/370 |
| 4,394,151 | 7/1983 | deFraine et al. | 71/76 |
| 4,427,673 | 1/1984 | Kramer et al. | 514/383 |
| 4,482,558 | 11/1984 | Richardson et al. | 514/383 |
| 4,503,063 | 3/1985 | Richardson et al. | 514/383 |
| 4,507,140 | 3/1985 | Sugavanam | 548/262 |
| 4,517,194 | 5/1985 | Kunz et al. | 548/262 |
| 4,568,752 | 2/1986 | Fryberg | 548/139 |
| 4,663,463 | 5/1987 | Kunz et al. | 548/262 |
| 4,713,379 | 12/1987 | Kramer et al. | 514/212 |
| 4,715,887 | 12/1987 | Kramer et al. | 71/92 |

FOREIGN PATENT DOCUMENTS

| 0054974 | 6/1982 | European Pat. Off. | 548/341 |
|---|---|---|---|
| 0055833 | 7/1982 | European Pat. Off. | 548/341 |
| 60223 | 9/1982 | European Pat. Off. | 548/262 |
| 0069448 | 1/1983 | European Pat. Off. | 514/383 |
| 84236 | 7/1983 | European Pat. Off. | 548/262 |
| 115400 | 8/1984 | European Pat. Off. | 514/383 |
| 2104065 | 3/1983 | United Kingdom | 548/262 |
| 2114120 | 8/1983 | United Kingdom | 548/262 |
| 2120235 | 11/1983 | United Kingdom | 548/262 |

Primary Examiner—Mary C. Lee
Assistant Examiner—Patricia L. Morris
Attorney, Agent, or Firm—Peter C. Richardson; J. Trevor Lumb; Gregg C. Benson

[57] ABSTRACT

Compounds of the formula

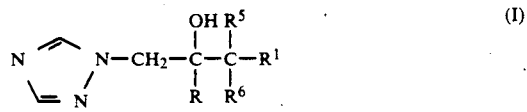

or a pharmaceutically or agriculturally acceptable acid addition salt thereof, wherein R is 5-chloro-2-pyridyl, or phenyl optionally substituted by one to three substituents, each independently selected from F, Cl, Br, I, $CF_3$, $C_1$-$C_4$alkyl and $C_1$-$C_4$alkoxy; $R^1$ is CN, $CSNH_2$ or $CONR^2R^3$ where either (a) $R^2$ is H or certain alkyl groups and $R^3$ is H or certain alkyl, substituted alkyl, aralkyl, phenyl or cycloalkyl groups, or (b) $R^2$ and $R^3$ taken together with the nitrogen atom to which they are attached form a nitrogen heterocyclic group, optionally containing an oxygen atom or $NR^4$ group, as a ring member and $R^4$ is H, $C_1$-$C_4$alkyl; $C_2$-$C_4$alkanoyl or ($C_1$-$C_4$alkoxy)carbonyl;

$R^5$ and $R^6$ are each H or $CH_3$; methods for their use in combatting fungal infections in plants, seeds and animals, including humans, pharmaceutical and agricultural compositions containing them and intermediates therefor.

13 Claims, No Drawings

3-ARYL-3-HYDROXY-4-(1H-1,2,4-TRIAZOL-1-YL)BUTYRAMIDE AND DERIVATIVES AS ANTIFUNGAL AGENTS

CROSS REFERENCE TO RELATED APPLICATIONS

This is a continuation-in-part of application Ser. No. 808,390, filed Nov. 29, 1985, now abandoned, which is a continuation of application Ser. No. 535,973, filed Sept. 26, 1983, now abandoned.

BACKGROUND OF THE INVENTION

This invention relates to novel triazole derivatives which have antifungal activity and are useful in the treatment of fungal infections in animals, including humans, and as agricultural fungicides.

Published United Kingdom Patent Application GB 2,104,065A discloses compounds of the formula

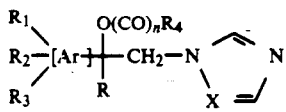

where, inter alia, X is N, n is O, Ar is phenyl, $R_1$, $R_2$, $R_3$ are each H, halogen, $C_1$-$C_3$alkyl or $C_1$-$C_3$alkoxy; $R_4$ is H, and R is $COOR_5$, $COSR_6$, $CONR_7R_8$ or CN; and $R_7$ and $R_8$ are each H, $C_1$-$C_6$alkyl, $C_3$-$C_7$cycloalkyl, phenyl or benzyl. The compounds are disclosed as useful in combating or preventing infestations of plants by microorganisms. There is no disclosure of human utility for these compounds.

U.S. Pat. No. 4,394,151 issued July 19, 1983 relates to fungicides and plant growth regulators of the general formula

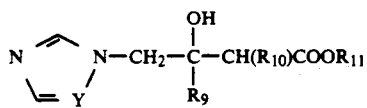

where, inter alia, Y is N, $R_9$ is optionally substituted phenyl, $R_{10}$ is H or alkyl and $R_{11}$ is H, alkyl, cycloalkyl, optionally substituted phenyl or optionally substituted benzyl or $R_9$ and $R_{10}$ taken together form a lactone. Here again, no disclosure of human utility is set forth.

European Patent Application No. 69,448 discloses compounds of the formula

where, inter alia, X is triazolyl, $R_{12}$ and $R_{13}$ are each optionally substituted phenyl provided that at least one of $R_{12}$ and $R_{13}$ contains at least one substituent; $R_{14}$ and $R_{15}$ are each H, alkyl, cycloalkyl, alkoxyalkyl, hydroxyalkyl, aminoalkyl, carboxyalkyl, phenyl or benzyl or, taken together with the nitrogen atom to which they are attached, they form a pyrrolidinyl, morpholino or a 4-substituted piperazino group. They are stated to be useful in treatment of fungal infections in plants, seeds and animals including humans.

European Patent Application No. 54974 discloses imidazole derivatives of the formula

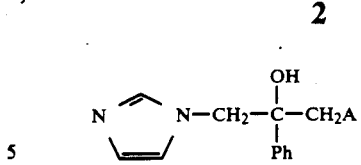

where Ph is phenyl optionally substituted with halogen and A is e.g., $NR_{16}R_{17}$ where $R_{16}$ and $R_{17}$ are each H, alkyl, cycloalkyl, or taken together with the adjacent nitrogen atom they form certain rings. They are stated to be useful as antifungal agents for humans.

SUMMARY OF THE INVENTION invention, there are provided compounds of the formula

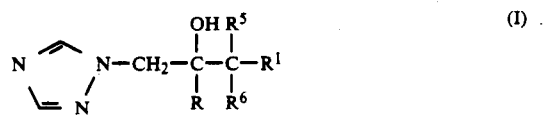

(I)

where

R is phenyl optionally substituted by 1 to 3 substituents each independently selected from F, Cl, Br, I, $CF_3$, $C_1$-$C_4$alkyl and $C_1$-$C_4$alkoxy, or R is a 5-chloropyrid-2-yl group;

$R^1$ is —CN, —CSNH$_2$, or —CONR$^2$R$^3$ where either (a) $R^2$ is H or $C_1$-$C_6$alkyl, and $R^3$ is H, $C_1$-$C_6$alkyl, benzyl, phenethyl, phenyl, —CH$_2$CF$_3$, adamantyl, pyridylmethyl, $C_3$-$C_7$carbamoylmethyl, ($C_2$-$C_4$alkenyl)methyl, 2-hydroxyethyl, 2-(dimethylamino)ethyl, 2-(methylthio)ethyl, 2-(methylsulphinyl)ethyl, 2-(methylsulphonyl)ethyl or 2-phenoxyethyl; said benzyl, phenethyl, phenyl and phenoxy groups being optionally ring-substituted by 1 or 2 substituents each independently selected from $C_1$-$C_4$alkyl, $C_1$-$C_4$alkoxy, F, Cl, Br, I and $CF_3$, (b) $R^2$ and $R^3$ taken together with the nitrogen atom to which they are attached represent a group of the formula

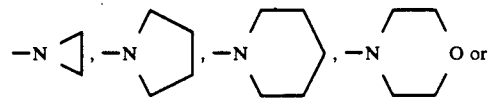

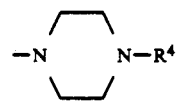

where $R^4$ is H, $C_1$-$C_4$alkyl, $C_2$-$C_4$alkanoyl or ($C_1$-$C_4$alkoxy)carbonyl; $R^5$ and $R^6$ are each H or $CH_3$; and their pharmaceutically and agriculturally acceptable salts, especially their acid addition salts.

The invention also provides a pharmaceutical composition comprising an antifungal amount of a compound of the formula (I) or pharmaceutically acceptable acid addition salt thereof, together with a pharmaceutically acceptable diluent or carrier.

The invention further provides a compound of the formula (I) or pharmaceutically acceptable acid addition salt thereof, for use in treating fungal infections in animals, including humans.

The invention also includes an agricultural composition suitable for use on a plant or seed comprising an antifungal amount of a compound of formula (I) or agriculturally acceptable acid addition salt thereof, together with an agriculturally acceptable diluent or carrier.

Yet further, the invention provides a method of treating an animal, including a human being, having a fungal infection, which comprises administering to the animal an antifungal effective amount of a compound of the formula (I) or pharmaceutically acceptable acid addition salt thereof.

The invention also includes a method of treating a seed or plant having a fungal infection, which comprises administering to the plant or seed, or to the locus of said plant, an antifungally effective amount of a compound of the formula (I) or of an agriculturally acceptable acid addition salt thereof.

When R is said phenyl group it is preferably phenyl substituted by 1 to 3 substituents, more preferably 1 or 2 substituents, each independently selected from F, Cl, Br, I and CF$_3$. Particularly preferred values of R include 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2,5-difluorophenyl, 2-fluoro-4-chlorophenyl, 2-chloro-4-fluorophenyl, 2,4,6-trifluorophenyl and 4-bromo-2,5-difluorophenyl.

Even more preferably R is 2,4-dichlorophenyl, 4-chlorophenyl or 2,4-difluorophenyl.

R is most preferably 2,4-dichlorophenyl or 2,4-difluorophenyl.

Particularly preferred as R$^1$ are —CN, —CSNH$_2$, or CONR$^2$R$^3$ wherein either (a) R$^2$ is H, CH$_3$ or C$_2$H$_5$, and R$^3$ is H, C$_1$-C$_6$alkyl, p-chlorobenzyl, p-chlorophenethyl, p-methylphenethyl, —CH$_2$CF$_3$, 1-adamantyl, 4-pyridylmethyl, cyclopropyl, carbamoylmethyl, —CH$_2$.CH=CH$_2$, 2-hydroxyethyl, 2-(dimethylamino)ethyl, 2-(methylthio)ethyl, 2-(methylsulphinyl)ethyl, 2-(methylsulphonyl)ethyl, p-chlorophenyl or 2-(p-chlorophenoxy)ethyl; or (b) R$^2$ and R$^3$ taken together with the nitrogen atom to which they are attached represent a group of the formula:

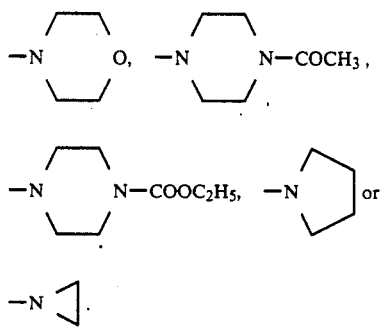

R$^1$ is more preferably —CONH$_2$ or —CONH(C$_1$-C$_4$alkyl), most preferably —CONH$_2$, —CONH.CH$_3$ or —CONH.C$_2$H$_5$.

R$^5$ and R$^6$ are each preferably H.

In the most preferred individual compounds, R is 2,4-dichlorophenyl or 2,4-difluorophenyl; R$^1$ is —CONH$_2$, —CONHCH$_3$ or —CONHC$_2$H$_5$; and R$^5$ and R$^6$ are H.

In one aspect of the invention, there are provided compounds of the formula:

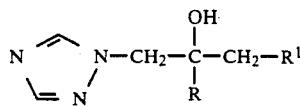

where

R is phenyl optionally substituted by 1 to 3 substituents each independently selected from F, Cl, Br, I, CF$_3$, C$_1$-C$_4$alkyl and C$_1$-C$_4$alkoxy, or R is a 5-chloro-pyrid-2-yl group; and R$^1$ is —CN or —CONR$^2$R$^3$ where R$^2$ is H, or C$_1$-C$_6$alkyl, and R$^3$ is H, C$_1$-C$_6$alkyl, benzyl, —CH$_2$CF$_3$ or adamantyl, said benzyl group being optionally substituted on its phenyl ring portion by 1 or 2 substituents each independently selected from C$_1$-C$_4$alkyl, C$_1$-C$_4$alkoxy, F, Cl, Br, I and CF$_3$, or R$^2$ and R$^3$ taken together with the nitrogen atom to which they are attached represent a group of the formula

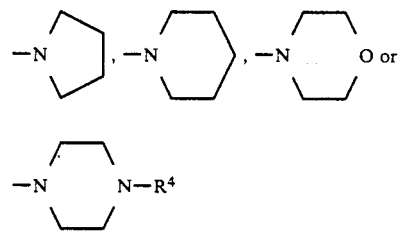

where R$^4$ is H, C$_1$-C$_4$alkyl, C$_2$-C$_4$alkanoyl or (C$_1$-C$_4$alkoxy)carbonyl; and their pharmaceutically acceptable salts.

In another aspect of the invention, there are provided compounds of the formula:

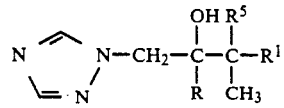

where R is phenyl optionally substituted by 1 to 3 substituents each independently selected from F, Cl, Br, I, CF$_3$, C$_1$-C$_4$alkyl and C$_1$-C$_4$alkoxy, or R is a 5-chloro-pyrid-2-yl group; R$^1$ is —CN or —CONR$^2$R$^3$ where R$^2$ is H, or C$_1$-C$_6$alkyl, and R$^3$ is H, C$_1$-C$_6$alkyl, benzyl, —CH$_2$CF$_3$ or adamantyl, said benzyl group being optionally substituted on its phenyl ring portion by 1 or 2 substituents each independently selected from C$_1$-C$_4$alkyl, C$_1$-C$_4$alkoxy, F, Cl, Br, I and CF$_3$, or R$^2$ and R$^3$ taken together with the nitrogen atom to which they are attached represent a group of the formula

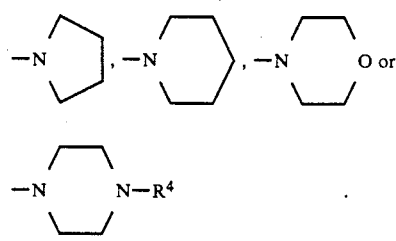

where R$^4$ is H, C$_1$-C$_4$alkyl, C$_2$-C$_4$alkanoyl or (C$_1$-C$_4$alkoxy)carbonyl; and R$^5$ is H or CH$_3$; and their pharmaceutically acceptable salts.

Where the compounds of formula (I) contain at least one chiral center, the invention includes both the resolved and unresolved forms.

The invention also includes the novel intermediates of the formula:

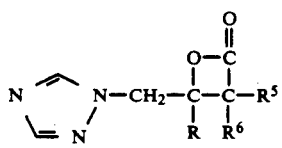
(A)

where R, $R^5$ and $R^6$ are as previously defined for formula (I).

Other useful intermediates have the formula:

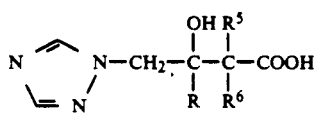
(B)

where R, $R^5$ and $R^6$ are as defined for formula (I).

DETAILED DESCRIPTION OF THE INVENTION

The compounds of formula (I) are prepared, for example, as illustrated below.

(1) Compounds in which $R^1$ is —CN and $R^5$ and $R^6$ are H are prepared by the following general method:

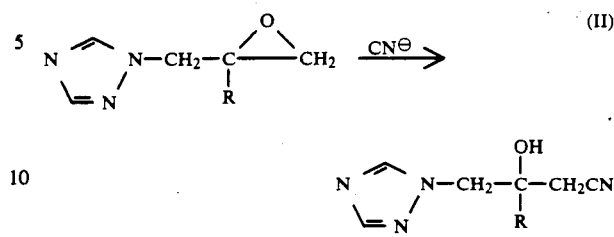

The preferred source of cyanide ions are the alkali metal cyanides, particularly sodium and potassium cyanide. In a typical procedure, the compound (II) and sodium or potassium cyanide are heated together in a suitable organic solvent, e.g. dimethylformamide, at up to 100° C., preferably 65°–70° C., for up to 6 hours. It is preferred to add the cyanide dropwise to the solution of the oxirane over about a half-hour. After cooling the reaction mixture and pouring it into water, the desired product is isolated and purified by conventional techniques.

The starting materials of the formula (II) are in many cases known compounds (see e.g., European Patent Application Publication No. 44605) or can be prepared by routine methods as will be known to those skilled in the art, for example,

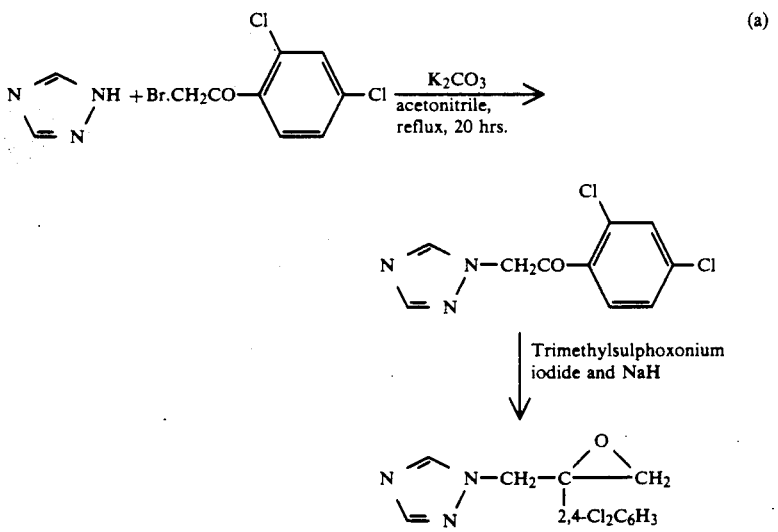

or

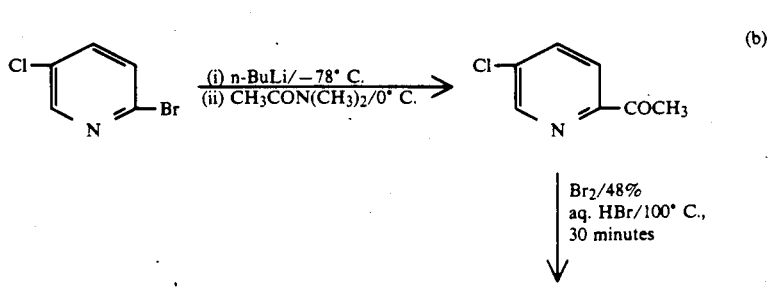

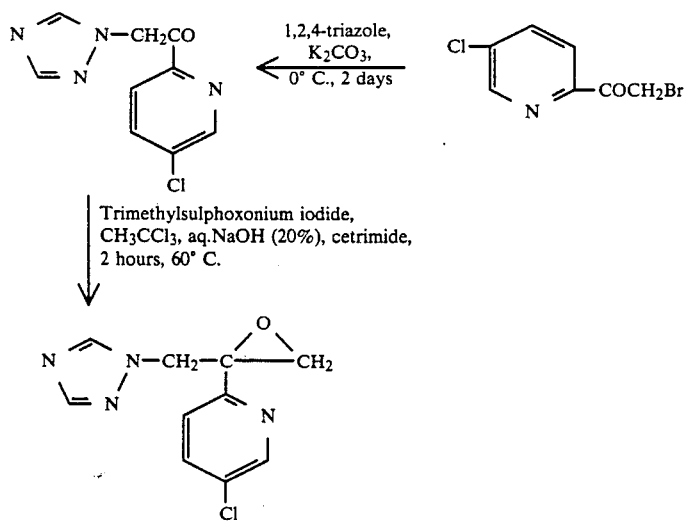

(2) Compounds in which $R^1$ is —CN and $R^5$ and $R^6$ are each H or $CH_3$ are prepared, for example, by the following general route

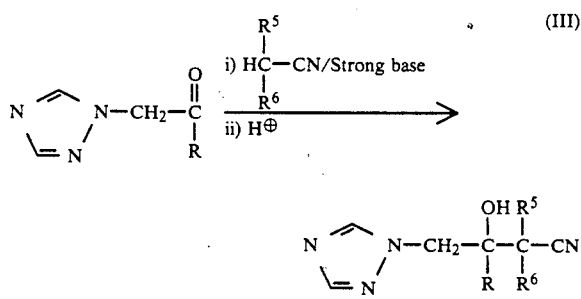

The preferred strong base in n-butyllithium. In a typical procedure, the nitrile is dissolved in a suitable solvent, e.g., dry tetrahydrofuran (THF), and the resulting solution is then cooled to about −70° C. A solution of n-butyllithium in hexane is then slowly added dropwise. After stirring for about an hour at −70° C., the ketone (III) in a suitable solvent, e.g., dry THF, is slowly added dropwise. After stirring for about an hour at −70° C. glacial acetic acid in a little THF is added and the reaction mixture is allowed to warm to 0° C. The product is then isolated and purified conventionally. When one of $R^5$ and $R^6$ is H and the other is $CH_3$, the product will exist in two diastereoisomeric forms and these are often separated by chromatography.

The starting materials of the formula (III) are either known compounds or can be prepared by conventional methods.

(3) Compounds in which $R^1$ is —$CONH_2$ and $R^5$ and $R^6$ are H are prepared, for example, as follows:

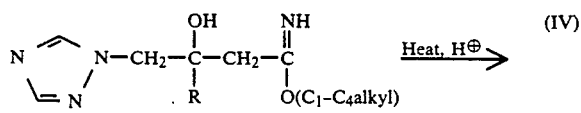

Preferable compound (IV) is used in its ethyl ester form. The acid is preferably supplied by using compound (IV) in an acid addition salt form, e.g. as the dihydrochloride. Alternatively, the free base is used and hydrogen chloride gas bubbled into the solution to form the salt. Typically the reactants are heated together for a short period, preferably under reflux, in a suitable high-boiling organic solvent such as 1,2-dichlorobenzene (b.p. 178° C.), the reaction is usually complete in about 15 minutes.

The starting materials of the formula (IV) are obtainable conventionally, e.g. as follows:

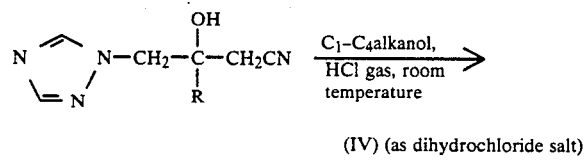

(IV) (as dihydrochloride salt)

(4) Compounds in which $R^1$ is —$CONH(C_1-C_4alkyl)$ or —$CON(C_1-C_4alkyl)_2$ are prepared by the alkylation of the corresponding starting materials in which $R^1$ is —$CONH_2$. The alkylation is typically carried out by dissolving the starting material in a suitable organic solvent, e.g. dry THF, followed by cooling to 0°-5° C. A strong base such as sodium hydride is then added. After stirring for a few minutes, an appropriate quantity of alkylating agent is added. The preferred alkylating agents are the alkali metal iodides and bromides. For mono-alkylation, only one equivalent of alkylating agent should be used, and, for dialkylation, at least 2 equivalents. The alkylated product is isolated from the reaction mixture by conventional techniques.

(5) Compounds in which $R^1$ is —$CONR^2R^3$ where $R^2$ $R^3$ are as defined in (a) or (b) in formula (I) can also be prepared as follows:

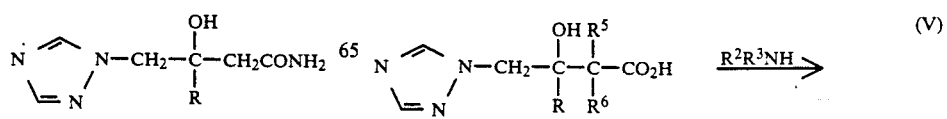

-continued

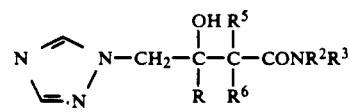

Compound (V) is preferably used in the form of its functional equivalent as an acylating agent, e.g. as an acid chloride or bromide, a mixed anhydride of the formula

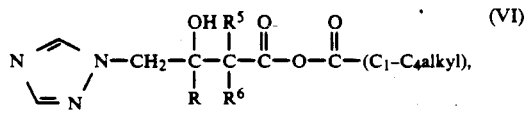

or as a $C_1$-$C_4$alkyl, succinimido, phthalimido or benzotriazol-1-yl ester.

All these functional equivalents are prepared conventionally from the acid (V). The acid chlorides and bromides are, for example, prepared by reaction of the acid of formula (V) with thionyl chloride or bromide, the mixed anhydrides by reaction with a $C_2$-$C_5$alkanoyl chloride, the $C_1$-$C_4$alkyl esters by simple esterification, and the succinimido, phthalimido and benzotriazol-1-yl esters by reaction with N-hydroxysuccinimide, N-hydroxyphthalimide or 1-hydroxybenzotriazole in the presence of a dehydrating agent such as dicyclohexylcarbodiimide.

In fact, it is preferred to use the compounds (V) in the form of their succinimido esters of the formula:

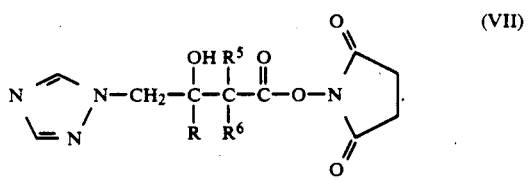

Thus in a typical procedure, dicyclohexylcarbodiimide dissolved in e.g. dry dioxan is added to a solution of the acid (V) and N-hydroxysuccinimide in e.g. dry dioxan. After stirring for a few hours at room temperature and filtering, the reaction is generally completed by stirring the solution of the compound (VII) with the amine $R^2R^3NH$ at room temperature for a few hours in e.g. dry dioxan, after which the product is isolated and purified by conventional means.

If compound (V) is reacted in its free acid form, the reaction should generally be carried out in the presence of a dehydrating agent such as dicyclohexylcarbodiimide.

The $C_1$-$C_4$alkyl esters can also be prepared as follows:

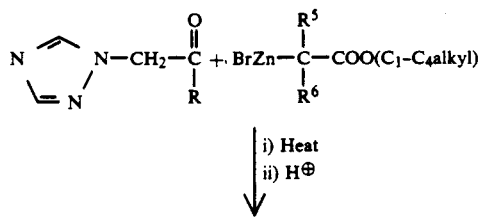

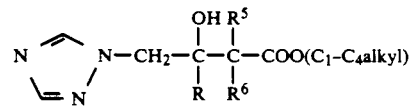

Generally some of the product (VIII) cyclises in situ under the reaction conditions to give the intermediate lactone (A). Mixtures of the ester (VIII) and lactone (A) are separated e.g. by column chromatography.

The benzotriazol-1-yl esters have the formula:

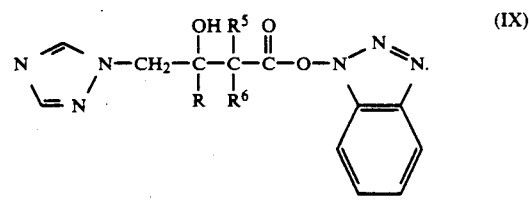

These are prepared as discussed above.

Thus in a typical procedure, dicyclohexylcarbodiimide, 1-hydroxybenzotriazole and the acid (V) are stirred together at room temperature for a short period in e.g. dry dioxan. The reaction is generally completed by stirring the resulting imtermediate (IX) with the amine $R^2R^3NH$ at room temperature until the reaction is complete, after which the product is isolated and purified by conventional means.

(6) Compounds of the formula (I) in which $R^1$ is —$CONH_2$ are prepared by the controlled hydrolysis of the corresponding compounds in which $R^1$ is —CN. Typically this hydrolysis is carried out by heating the starting nitrile at about 70°-100° C., preferably 90°-95° C., with aqueous sulphuric acid, preferably 80%, by weight, until the formation of the amide is complete as monitored by thin-layer chromatography.

Further hydrolysis to convert —$CONH_2$ to —COOH, if desired, is carried out under similar conditions. The compounds in which $R^1$ is —COOH are useful intermediates (see route (5) above, for example).

(7) The amides of the formula (I) in which $R^1$ is —$CONR^2R^3$ where $R^2$ and $R^3$ are as defined in (a) or (b) for formula (I) are also prepared from the intermediates of the formula (A) as follows:

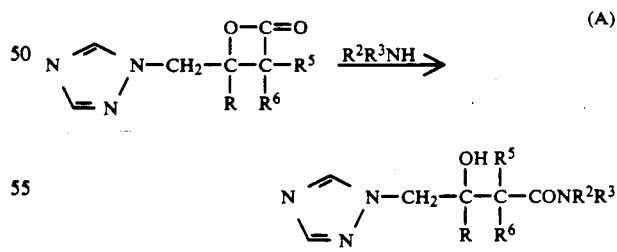

where R, $R^2$, $R^3$, $R^5$ and $R^6$ are as defined for formula (I).

The reaction is carried out by stirring the reactants together in a suitable solvent, e.g. ethanol, at room temperature until the reaction is complete. If necessary, the mixture is heated to accelerate the reaction. The product is then isolated and purified conventionally.

(8) Compounds in which $R^3$ is 2-(methylsulphinyl)ethyl and 2-(methylsulphonyl)ethyl are prepared e.g. by the oxidation of the corresponding 2-(methylthio)ethyl compounds using the appropriate quantity of oxidizing agent, e.g. m-chloroperbenzoic acid, in conventional manner.

(9) Compounds in which $R^1$ is —$CSNH_2$ are prepared e.g. as outlined below:

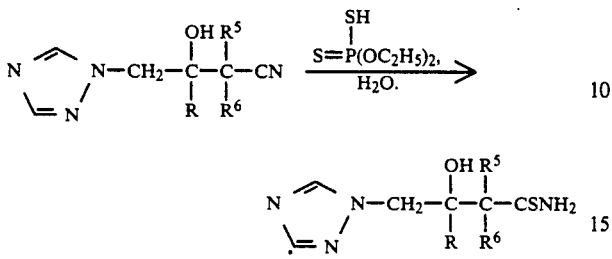

The reaction is typically carried out by heating the reactants at up to about 100° C. in the presence of water. The product is then isolated by conventional methods.

(10) Compounds in which $R^1$ is —$CONH_2$ and $R^5$ and $R^6$ are H are also prepared as shown below:

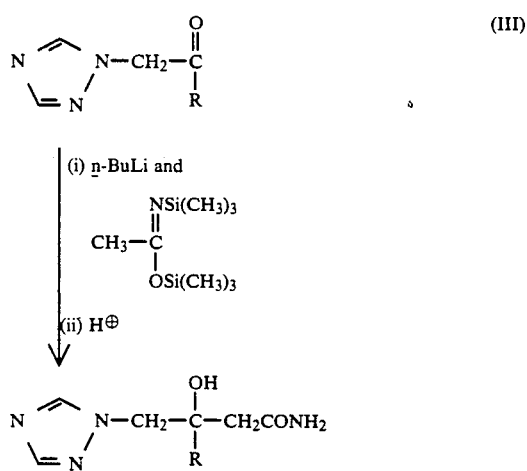

The reaction is typically carried out by stirring bis(-trimethylsilyl)acetamide at −70° C. in dry tetrahydrofuran (THF) while n-butyllithium is slowly added dropwise. The resulting solution is stirred at about −70° C. for a short period, then the ketone (III) in e.g. dry THF is slowly added, and the resulting mixture stirred at about −70° C. for a few hours. The reaction mixture is then allowed to warm to room temperature and aqueous acid is added. The product is then isolated and purified conventionally.

(11) Amides of formula (I) in which $R^2$ and $R^3$ together with the nitrogen atom to which they are attached represent aziridinyl are prepared e.g. as follows:

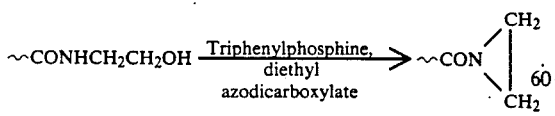

The reaction is generally carried out at room temperature in the presence of an organic solvent, e.g. dry tetrahydrofuran.

(12) The lactone intermediates of the formula (A) are prepared by cyclization, preferably using an ester, according to the following scheme:

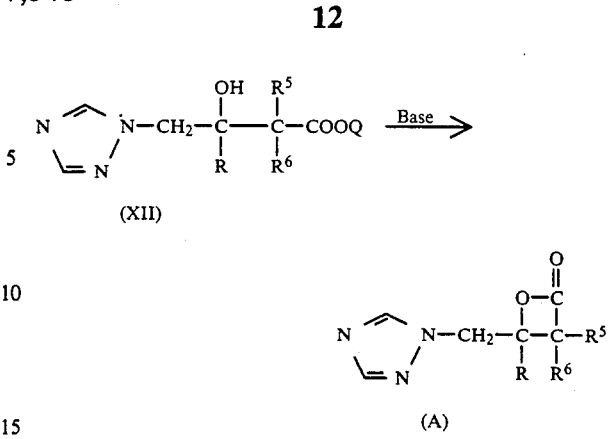

where $Q = C_1-C_2$ alkyl, phthalimido, succinimido or 1-benzotriazolyl.

These esters are prepared as previously described. The cyclization is carried out e.g. in the presence of a suitable base by stirring at room temperature. Preferred bases are tertiary amine bases, e.g. triethylamine, and alkali metal hydrides, e.g. sodium hydride.

The compounds of the invention contain a chiral center or centers and the invention includes both the resolved and unresolved forms.

Pharmaceutically acceptable acid addition salts of the compounds of the formula (I) are those formed from strong acids which form non-toxic acid addition salts, such as hydrchloric, hydrobromic, sulfuric, oxalic and methanesulfonic acids.

The salts are obtained by conventional procedures, e.g., by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their pharmaceutically acceptable salts are antifungal agents, useful in combating fungal infections in animals, including humans For example, they are useful in treating topical fungal infections in man caused by, among other organisms, species of Candida, Trichophyton, Microsporum or Epidermophyton, or in mucosal infections caused by *Candida albicans* (e.g., thrush and vaginal candidiasis). They are also useful in the treatment of systemic fungal infections caused by, for example, *Candida albicans, Cryptococcus neoformans, Aspergillus fumigatus*, Coccidioides, Paracoccidioides, Histoplasma or Blastomyces.

The in vitro evaluation of the antifungal activity of the compounds is carried out, e.g., by determining the minimum inhibitory concentration (m.i.c.), which is the concentration of the test compound in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests include, e.g., *Cryptococcus neoformans, Aspergillus fumigatus, Trichophyton* spp; *Microsporum* spp; *Epidermophyton floccosum, Coccidioides immitis* and *Torulopsis glabrata*.

The in vivo evaluation of the compounds is carried out, e.g., at a series of dose levels by intraperitoneal or intravenous injection or by oral administration to mice which are inoculated with a strain of *Candida albicans*. Activity is based on the survival of a treated group of mice after the death of an untreated group of mice following 48 hours observation. The dose level at which the compound provides 50% protection (PD$_{50}$) against the lethal effect of the infection is noted.

The in vivo oral PD$_{50}$ values for selected compounds of the invention, obtained with mice inoculated with a lethal dose of *Candida albicans* by the method described above, are summarized in the table below. Values in parenthesis were obtained in separate determinations

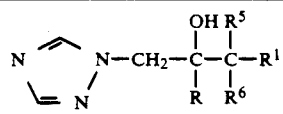
(I)

where R = 2,4-Cl$_2$C$_6$H$_3$—, R$^5$ = R$^6$ = H:

| R$^1$ | Example No. | Oral PD$_{50}$ (mg/kg) |
|---|---|---|
| CN | 1, 2 | 1.3 (1.3) |
| CONH$_2$ | 4, 44, 45 | 0.2 (0.2) (0.2) |
| CONHCH$_3$ | 5, 7, 43B | 0.2 (~0.4) (0.2) |
| CON⟨morpholino⟩ | 6 | ~20 |
| CONHCH(CH$_3$)$_2$ | 8 | 0.1 |
| CON(CH$_3$)$_2$ | 9 | 0.4 |
| CONHCH$_2$—C$_6$H$_4$—Cl | 10 | 0.1 |
| CON⟨piperazinyl-NCOCH$_3$⟩ | 11 | ~30 |
| CON⟨piperazinyl-NCO$_2$C$_2$H$_5$⟩ | 12 | 3.1 |
| CON⟨pyrrolidinyl⟩ | 13 | ~40 |
| CON(C$_2$H$_5$)$_2$ | 14 | 0.4 |
| CONHC$_2$H$_5$ | 15 | 0.2 |
| CONH(1-admantyl) | 16 | ~20 |
| CONHCH$_2$-4-pyridyl | 17 | 1.5 |
| CONHCH$_2$CF$_3$ | 18 | 0.4 |
| CONH(CH$_2$)$_5$CH$_3$ | 19 | 2.2 |
| CONH-cyclopropyl | 20 | 0.1 |
| CONHCH$_2$CH$_2$-4-ClC$_6$H$_4$ | 21 | 0.6 |
| CONH(CH$_2$)$_2$CH$_3$ | 22 | 0.2 |
| CONHCH$_2$CH=CH$_2$ | 24 | 0.4 |
| CONHCH$_2$C(CH$_3$)$_3$ | 25 | 3.5 |
| CONHCH$_2$CH$_2$OH | 26 | 2.2 |
| CONH(CH$_2$)$_2$-4-CH$_3$C$_6$H$_4$ | 27 | 4.2 |
| CONH(CH$_2$)$_2$N(CH$_3$)$_2$ | 28 | 4.2 |
| CONH—C$_6$H$_4$—Cl.C$_6$H$_{12}$ | 29 | 4.2 |
| CONHCH$_2$CH$_2$SCH$_3$ | 30 | 0.1 |
| CONH(CH$_2$)$_2$O—C$_6$H$_4$—Cl | 31 | 3.1 |
| CON(CH$_3$)CH(CH$_3$)$_2$ | 32 | 0.2 |
| CONHCH$_2$CH$_2$S(O)CH$_3$ | 47 | 0.2 |
| CONHCH$_2$CH$_2$S(O$_2$)CH$_3$ | 48 | 0.1 |
| CON⟨aziridinyl⟩ | 49 | 4.2 |
| CSNH$_2$ | 50 | 0.5 |

| R$^1$ | R | R$^5$ | R$^6$ | Example No. | Oral PD$_{50}$ (mg/kg) |
|---|---|---|---|---|---|
| CONHCH$_3$ | 2,4-F$_2$C$_6$H$_3$ | H | H | 33 | 0.3 |
| CN | 2,4-Cl$_2$C$_6$H$_3$ | H | CH$_3$ | 34 | 0.1 |
| CN | 4-ClC$_6$H$_4$ | H | CH$_3$ | 35 | 2.0 |
| CONH$_2$ | 2,4-Cl$_2$C$_6$H$_3$ | H | CH$_3$ | 37 | 0.4 |
| CONH$_2$ | 2,4-F$_2$C$_6$H$_3$ | H | CH$_3$ | 38 | 0.4 |
| CONH$_2$ | 4-ClC$_6$H$_4$ | H | CH$_3$ | 39 | 0.5 |
| CONHCH$_3$ | 2,4-Cl$_2$C$_6$H$_3$ | H | CH$_3$ | 40 | 0.2 |
| CONH$_2$ | 2,4-Cl$_2$C$_6$H$_3$ | CH$_3$ | CH$_3$ | 41D | 3.1 |
| CONHCH$_3$ | 2,4-Cl$_2$C$_6$H$_3$ | CH$_3$ | CH$_3$ | 42 | 0.6 |

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral or parenteral administration to human patients, the daily dosage level of the antifungal compounds of the formula (I) will be from 0.1 to 5 mg/kg (in divided doses) when administered by either the oral or parenteral route. Thus tablets or capsules of the compounds will contain from 5 mg. to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) are administered in the form of a suppository or pessary, or they are applied topically in the form of a lotion, solution, cream, ointment or dusting powder. For example, they are incorporated into a cream consisting of an aqueous emulsion of polyethylene glycols or liquid paraffin; or incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rust, mildews and molds, and the compounds are thus useful for treating plants and seeds to eradicate or prevent such diseases.

The in vitro evaluation of the activity of the compounds against plant fungi is determined, e.g., by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds are applied in the form of dusting powders, or granules, seed dressings, aqueous solutions, dispersions or emulsions, dips, sprays, aerosols or smokes. Compositions are also applied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example, they are applied directly to the plant foilage, stems, branches, seeds or roots or to the soil or other growing medium, and they can be used not only to eradicate disease, but also prophylactically to protect the plants or seeds from attack.

The following Examples illustrate the invention. All temperatures are in ° C. Mixtures of solvents employed for chromatography are by volume.

EXAMPLE 1

1-Cyano-2-(2,4-dichlorophenyl)-3-(1H-1,2,4-triazol-1-yl)propan-2-ol

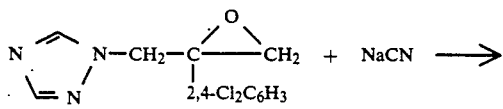

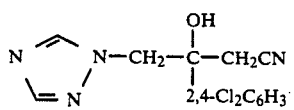

To 2-(2,4-Dichlorophenyl)-2-(1H-1,2,4-triazol-1-ylmethyl)oxirane (6.7 g) in dimethylformamide (198 ml) at 60° C. was added dropwise over 25 minutes a solution of sodium cyanide (2.84 g) in water (49 ml). Heating at 60° C. was continued for five hours. The reaction mixture was then cooled, poured into water (900 ml), and extracted with ethyl acetate (3×150 ml). The combined organic extracts were washed with saturated aqueous brine, dried ($Na_2SO_4$) and evaporated to dryness to give a pale yellow solid (6.1 g) which was triturated with ethyl ether. The residual solid was recrystallized from ethyl ether/methanol to give the title compound, 4.13 g (56%), m.p. 217°-219° C.

Analysis %:
Found: C, 48.3; H, 3.4; N, 18.4.
Calculated for $C_{12}H_{10}Cl_2NO$: C, 48.5; H, 3.4; N, 18.8.

EXAMPLE 2

1-Cyano-2-(2,4-dichlorophenyl)-3-(1H-1,2,4-triazol-1-yl)propan-2-ol

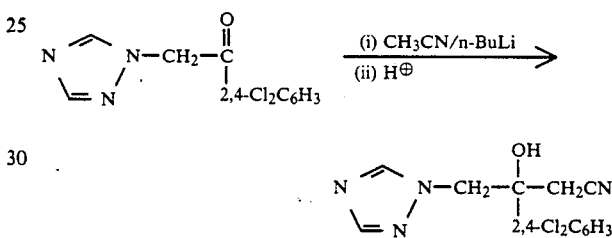

Acetonitrile (2.25 g, 0.055 mole) was dissolved in dry tetrahydrofuran (100 ml) and the resulting solution was cooled to −70° C. under nitrogen in an acetone/dry ice bath. A solution of n-butyllithium in hexane (39 ml, 1.55 molar, 0.060 mole) was added dropwise over five minutes. After stirring for about 45 minutes at −70° C., 2′,4′-dichloro-2-(1H-1,2,4-triazol-1-yl)acetophenone (12.8 g) in dry tetrahydrofuran (100 ml) was added dropwise over a 15 minute period. Stirring was continued at −70° C. for about one hour and then glacial acetic acid (20 ml) in tetrahydrofuran (20 ml) was added dropwise. The cooling bath was then removed. The reaction mixture was allowed to warm to 0° C., quenched in water (400 ml), and solid sodium carbonate was added to raise the pH to 8.0. After extraction with ethyl acetate (3×75 ml), the combined organic extracts were washed with saturated brine (3×50 ml), dried ($Na_2SO_4$) and evaporated to a pale yellow solid. This solid was washed well with ethyl ether to give the title compound (6.61 g, 44.5%), identical to the product of Example 1 as confirmed by n.m.r. and i.r. spectroscopy.

EXAMPLE 3

1-Cyano-2-(2,4-difluorophenyl)-3-(1H-1,2,4-triazol-1-yl)propan-2-ol was prepared similarly to the previous Example using 2′,4′-difluoro-2-(1H-1,2,4-triazol-1-yl)acetophenone as the starting ketone. It had an m.p. of 154°-155° C.

Analysis %:
Found C, 54.0; H, 3.8; N, 21.5.
Calculated for $C_{12}H_{10}F_2N_4O$: C, 54.6; H, 3.8; N, 21.2.

EXAMPLE 4

1-Carbamoyl-2-(2,4-dichlorophenyl)-3-(1H-1,2,4-triazol-1-yl)propan-2-ol

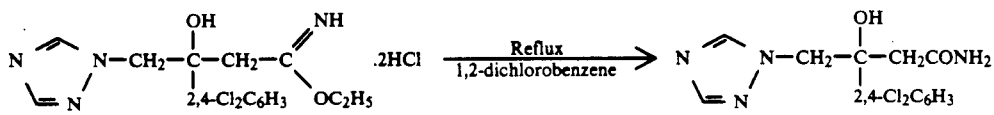 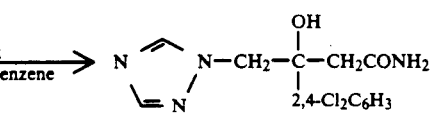

3-(2,4-Dichlorophenyl)-3-hydroxy-4-(1H-1,2,4-triazol-1-yl)butyrimidic acid, ethyl ester dihydrochloride (3.42 g) was suspended in 1,2-dichlorobenzene (35 ml) and the mixture was heated to the reflux temperature of the solvent [178° C.). After refluxing for five minutes, a solution was obtained. Refluxing was then continued for an additional 10 minutes. The reaction mixture was cooled, evaporated, and the resulting gum was triturated with hexane and heated with acetone. On cooling a cream-colored granular solid was formed which was filtered to yield the title compound as a solvate (1.26 g). On standing overnight in a refrigerator some further solvated product precipitated (0.62 g). After drying at 80° C. for 6 hours to remove the solvent the pure (unsolvated) title compound was obtained, yield 1.5 g, m.p. 144°–145° C.

Analysis % (after said drying):
Found: C, 45.5; H, 3.8; N, 17.5.
Calculated for $C_{12}H_{12}Cl_2N_4O_2$: C, 45.7; H, 3.8; N, 17.8.

EXAMPLE 5

2-(2,4-Dichlorophenyl)-1-(N-methylcarbamoyl)-3-(1H-1,2,4-triazol-1-yl)propan-2-ol

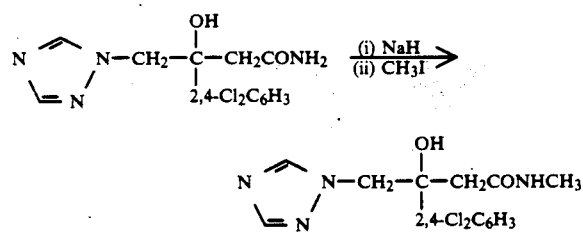

1-Carbamoyl-2-(2,4-dichlorophenyl)-3-(1H-1,2,4-triazol-1-yl)propan-2-ol (1.0 g) was dissolved in dry tetrahydrofuran (20 ml) and the reaction mixture was cooled to 0°–5° C. Sodium hydride (0.15 g, as a 50% dispersion in oil) was then added, the mixture stirred for 10 minutes and methyl iodide (0.45 g) added. Further quantities of methyl iodide (90 mg) and sodium hydride (375 mg, as a 50% dispersion in oil) were added. After stirring for a few minutes, yet further quantities of methyl iodide (90 mg) and sodium hydride (375 mg, as a 50% dispersion in oil) were added. The mixture was then quenched in water and extracted with ethyl acetate (3×50 ml). The combined organic extracts were dried (MgSO$_4$) and evaporated to give the crude product as a gum. A solution of this gum in methylene chloride (20 ml) was chromatographed on a silica gel column (10 g), eluting with methylene chloride (100 ml), then with methylene chloride containing 2% isopropanol and 0.2% NH$_4$OH (300 ml), and finally with methylene chloride containing 5% isopropanol and 0.5% NH$_4$OH (500 ml). Appropriate fractions were collected to yield the title compound, which was recrystallized from cyclohexane (yield 41 mg, m.p. 151°–154° C.).

Analysis %:
Found: C, 47.3; H, 4.35; N, 17.2.
Calculated for $C_{13}H_{14}Cl_2N_4O_2$: C, 47.4; H, 4.3; N, 17.0.

EXAMPLE 6

2-(2,4-Dichlorophenyl)-1-(morpholinocarbonyl)-3-(1H-1,2,4-triazol-1-yl)propan-2-ol monohydrate

A.

1-Carboxy-2-(2,4-dichlorophenyl)-3-(1H-1,2,4-triazol-1yl)propan-2-ol

1-Cyano-2-(2,4-dichlorophenyl)-3-(1H-1,2,4-triazol-1-yl)-2-propanol (4 g, 13.9 mmole) was dissolved in 40% aqueous sulfuric acid (100 ml) and heated in an oil bath at 100°–110° C. for 18 hours. The solution was then cooled, diluted with water (200 ml), and rendered alkaline by the slow addition of solid sodium bicarbonate. The mixture was then extracted several times with ethyl acetate (3×100 ml) and the aqueous phase was rendered acidic (pH 3) by the addition of dilute orthophosphoric acid. The aqueous phase was then extracted with ethyl ether (3×150 ml), the combined ether extracts were washed once with water, and then dried over magnesium sulfate. Evaporation of the ether gave the title compound as a pale yellow solid, 2.7 g, (62%), m.p. 158°–159° C.

Analysis %:
Found: C, 46.35; H, 3.5; N, 13.6.
Required for $C_{12}H_{11}Cl_2N_3O_3$: C, 45.6; H, 3.5; N, 13.3.

B

N,N'-Dicyclohexylcarbodiimide ("DCCD") (110 mg, 0.5 mmole) dissolved in dry dioxan (5 ml) was added to a solution of 1-carboxy-2-(2,4-dichlorophenyl)-3-(1H-1,2,4-triazol-1-yl)propan-2-ol (150 mg, 0.5 mmole) and N-hydroxysuccinimide ("NHS") (60 mg, 0.5 mmole) in dry dioxan (10 ml), and the mixture was stirred at room temperature for 2 hours. The precipitate was filtered off, washed with dry dioxan (10 ml) and the combined filtrate and washings were then added to a solution of morpholine (300 mg, 3.4 mmole) in dry dioxan (2 ml). The resultant solution was left at room temperature for 18 hours, diluted with ethyl acetate (100 ml), washed three times with saturated brine solution and dried over magnesium sulfate. Evaporation of the filtrate gave an oil (300 mg) which was then chromatographed on "Kieselgel 60H" (Merck, Trade Mark) silica (10 g), eluting with methylene chloride containing 2% isopropyl alcohol and 0.2% aqueous ammonium hydroxide (Sp. gr. 0.880). The title compound was obtained after evaporation of appropriate fractions as a colorless solid, 110 mg (57%), m.p. 92°–93° C.

Analysis %:
Found: C, 47.8; H, 4.7; N, 13.9.
Required for $C_{16}H_{18}N_4Cl_2O_3 \cdot H_2O$: 47.8; H, 5.0; N, 13.9.

EXAMPLES 7–32

The following compounds were prepared similarly to the previous Example, starting from the same acid, DCDD/NHS and the appropriate amine:

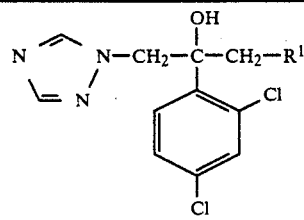

| Example No. | R¹ | m.p. (°C.) | Analysis % Theoretical in brackets | | |
|---|---|---|---|---|---|
| | | | C | H | N |
| 7 | —CONHCH₃ | 151–3° | (Identical to the product of Example 5) | | |
| 8 | —CONHCH(CH₃)₂ | 105–107° | 50.7 (50.6 | 5.2 5.1 | 15.3 15.7) |
| 9 | —CON(CH₃)₂ | 125–126.5° | 48.95 (49.1 | 4.65 4.7 | 16.3 16.4) |
| 10 | —CONHCH₂—⟨C₆H₄⟩—Cl | glass, 64–65° | 52.15 (52.05 | 3.95 3.9 | 12.5 12.8) |
| 11 | —CON⟨piperazinyl⟩NCOCH₃ | glass, 63–5° | (As trihydrate) 45.3 4.4 14.4 (45.1 5.6 14.6) | | |
| 12 | —CON⟨piperazinyl⟩NCO₂C₂H₅ | glass, 58–60° | (As hemihydrate) 49.2 5.1 15.0 (49.1 5.2 15.1) | | |
| 13 | —CON⟨pyrrolidinyl⟩ | glass, 40–41° | 52.4 (52.2 | 5.05 4.9 | 15.0 15.2) |
| 14 | —CON(C₂H₅)₂ | glass, 60–62° | 51.9 (51.8 | 5.5 5.4 | 15.0 15.1) |
| 15 | —CONHC₂H₅ | 129–130° | 49.0 (49.0 | 4.8 4.7 | 15.8 16.3) |
| 16 | —CONH(1-adamantyl) | 91–92° | 58.7 (58.8 | 6.1 5.8 | 12.0 12.5) |
| 17 | —CONHCH₂—⟨pyridyl⟩ | glass, 48–50° | (As hemihydrate) 52.3 4.2 16.5 (52.1 4.3 16.8) | | |
| 18 | —CONHCH₂CF₃ | glass, 60–62° | 42.6 (42.3 | 3.5 3.3 | 13.6 14.1) |
| 19 | —CONH(CH₂)₅CH₃ | 114–116° | 54.2 (54.1 | 6.1 6.1 | 14.1 14.0) |
| 20 | —CONH—⟨cyclopropyl⟩ | 122–123° | 50.6 (50.7 | 4.6 4.5 | 15.6 15.8) |

-continued

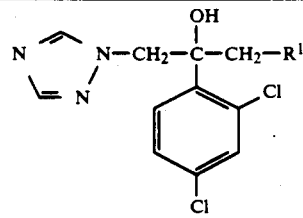

| Example No. | R[1] | m.p. (°C.) | C | H | N |
|---|---|---|---|---|---|
| | | | \multicolumn{3}{c}{Analysis % Theoretical in brackets} | | |
| 21 | —CONHCH₂CH₂—⟨C₆H₄⟩—Cl | 142–143° | 52.9 (52.9 | 4.2 4.2 | 12.2 12.3) |
| 22 | —CONH(CH₂)₂CH₃ | 169–170° | (As hydrochloride) 45.7 (45.8 | 4.8 4.9 | 14.0 14.2) |
| 23 | —CONHCH₂CONH₂ | 188–191° | (As hydrochloride hemihydrate) 40.6 (40.2 | 4.05 4.1 | 16.9 16.8) |
| 24 | —CONHCH₂—CH=CH₂ | glass | (As oxalate ½ hydrate) 45.4 (45.4 | 4.3 4.1 | 12.0 12.4) |
| 25 | —CONHCH₂C(CH₃)₃ | 135–137° | 53.2 (53.0 | 5.9 5.8 | 14.7 14.5) |
| 26 | —CONHCH₂CH₂OH | 143–145° | (As ¼ hydrate) 46.1 (46.2 | 4.4 4.6 | 15.3 15.4) |
| 27 | —CONH(CH₂)₂—⟨C₆H₄⟩—CH₃ | 144–145° | 58.2 (58.2 | 5.1 5.1 | 12.8 12.9) |
| 28 | —CONH(CH₂)₂N(CH₃)₂ | 107–110° | (As dihydrochloride dihydrate) 38.8 (38.8 | 5.2 5.1 | 13.6 14.2) |
| 29 | —CONH—⟨C₆H₄⟩—Cl. | 102–105° | (Contains 1 mole of cyclohexane) 56.6 (56.6 | 5.4 5.3 | 10.9 11.0) |
| 30 | —CONHCH₂CH₂SCH₃ | 154–156° | 42.6 (42.3 | 4.5 4.5 | 13.3 13.2) |
| 31 | —CONHCH₂CH₂O—⟨C₆H₄⟩—Cl | 137–9° | 51.0 (51.1 | 4.0 4.1 | 11.9 11.9) |
| 32 | —CON(CH₃)(CH[CH₃]₂) | 131–2° | 51.7 (51.8 | 5.3 5.4 | 15.2 15.1) |

EXAMPLE 33

The following compound was prepared by the procedure of Example 6, starting from 1-carboxy-2-(2,4-difluorophenyl)-3-(1H-1,2,4-triazol-1-yl)-propan-2-ol, "DCCD", "NHS" and methylamine:

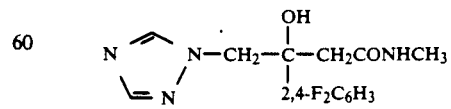

It melted at 129°–131° C.
Analysis %:
Found: C, 52.8; H, 4.9; N, 19.3.
Calculated for $C_{13}H_{14}F_2N_4O_2$: C, 52.7; H, 4.8; N, 18.9.

EXAMPLE 34

3-Cyano-2-(2,4-dichlorophenyl)-1-(1H-1,2,4-triazol-1-yl)butan-2-ol (2 diastereoisomeric forms)

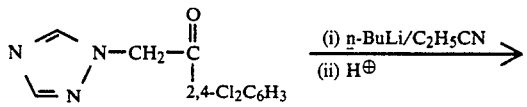

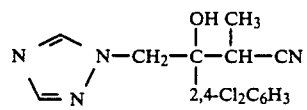

Propionitrile (1.21 g) in dry tetrahydrofuran (50 ml) was cooled to −72° C. A solution of n-butyllithium in n-hexane (14.2 ml, 1.55 molar) was then slowly added while maintaining the temperature of the reaction mixture at −45° C. or below. After stirring for about 30 minutes, 2-(1H-1,2,4-triazol-1-yl)-2',4'-dichloroacetophenone (2.56 g) in dry tetrahydrofuran (THF) (50 ml) was added slowly with stirring over a 20 minute period, the temperature of the mixture being maintained at −70° C. Stirring was continued at this temperature for one hour and then at −10° for a half hour, then glacial acetic acid (10 ml) in dry THF (15 ml) was added. The reaction mixture was allowed to warm to room temperature (20° C.), adjusted to pH 8 with solid sodium bicarbonate, and extracted with ethyl acetate (3×75 ml). The combined organic extracts were washed three times with water, dried (MgSO4), evaporated and ethyl ether (30 ml) was added to the residue, yielding a white crystalline solid and a yellow solution. The solid was filtered off, dissolved in a small volume of methylene chloride, and loaded onto an 18 g flash chromatography column of Merck's "Kieselgel 60" (Trade Mark) 230-400 mesh silica in ether (11×2 cm. diameter). Elution was carried out using 5% (by volume) acetone in ether at one p.s.i. (0.07 kg/m²) "Diastereoisomer 1" of the title compound was eluted first, 0.79 g, m.p. 178°-180° C.

Analysis %:
Found: C, 50.0; H, 3.8; N, 17.9.
Calculated for $C_{13}H_{12}Cl_2N_4O$: C, 50.2; H, 3.9; N, 18.0.

"Diastereoisomer 2" of the title compound was eluted next, 0.244 g, m.p. 202°-205° C.

Analysis %:
Found: C, 50.4; H, 3.9; N, 17.6.
Calculated for $C_{13}H_{12}Cl_2N_4O$: C, 50.2; H, 3.9; N, 18.0.

EXAMPLES 35 and 36

The following compounds were prepared similarly to the previous Example, starting from the appropriate acetophenone, n-BuLi/C2H5CN and glacial acetic acid.

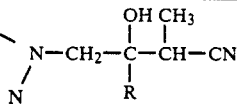

| Example No. | R | m.p. (°C.) | Analysis % Theoretical in Brackets | | |
|---|---|---|---|---|---|
| | | | C | H | N |
| 35 | 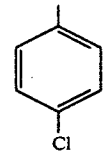 (mixture of diastereomers, not separated) | 159-162° | 56.4 (56.4 | 4.8 4.7 | 20.0 20.2) |
| 36 | (believed to be a mixture of diastereomers, not separated) | 185-187° | 56.2 (56.1 | 4.3 4.3 | 20.0 20.1) |

EXAMPLE 37

3-Carbamoyl-2-(2,4-dichlorophenyl)-1-(1H-1,2,4-triazol-1-yl)butan-2-ol hemihydrate and 3-carboxy-2-(2,4-dichlorophenyl)-1-(1H-1,2,4-triazol-1-yl)butan-2-ol 3-Cyano-2-(2,4-dichlorophenyl)-1-(1H-1,2,4-triazol-1-yl)butan-2-ol (700 mg, diastereoisomer 1 from the previous Example) was heated for 5½ hours at 90°-95° C. in 40% (by volume) aqueous sulfuric acid. The solution was then stirred at room temperature (20° C.) for 19 hours, after which time saturated aqueous sodium bicarbonate solution was added to raise the pH to 8.0. The solution was then extracted with ethyl acetate (3×50 ml). The combined organic extracts were washed with water, dried (MgSO4) and evaporated to yield the 3-carbamoyl title compound, 105 mg, m.p. 215°-217° C. after trituration with ethyl ether.

Analysis %: (3-carbamoyl compound)
Found: C, 46.8; H, 4.5; N, 15.5.
Calculated for $C_{13}H_{14}Cl_2N_4O_2 \cdot \frac{1}{2}H_2O$: C, 46.2; H, 4.5; N, 15.6.

The aqueous phases resulting from the ethyl acetate extractions were combined, acidified to pH 2.0 with dilute hydrochloric acid, and extracted with ethyl acetate (3×50 ml). The combined organic extracts were washed with water, dried (MgSO4) and evaporated to yield the title acid. After trituration with ethyl ether, the pure acid, 485 mg, m.p. 236°-238° C., was obtained.

Analysis %:
Found: C, 47.0; H, 3.9; N, 12.4.
Calculated for $C_{13}H_{13}Cl_2N_3O_3$: C, 47.3; H, 4.0; N, 12.7.

EXAMPLE 38

3-Carbamoyl-2-(2,4-difluorophenyl)-1-(1H-1,2,4-triazol-1-yl)butan-2-ol ¼ hydrate, m.p. 170°-172° C., was prepared similarly to the previous Example by the hydrolysis of the corresponding nitrile prepared in Example 36 but using 80% (w/w) aqueous sulfuric acid.

Analysis %:
Found: C, 52.0; H, 4.8; N, 18.5.
Calculated for $C_{13}H_{14}F_2N_4O_2 \cdot \frac{1}{4}H_2O$:
C, 51.9; H, 4.8; N, 18.6.

EXAMPLE 39

2-(4-Chlorophenyl)-3-carbamoyl-1-(1H-1,2,4-triazol-1-yl)butan-2-ol

The mixture of diastereomeric nitriles from Example 35 (3.9 g) was heated in sulfuric acid (80% by weight, 100 ml) for four hours at 60° C. The reaction mixture was then cooled, diluted with water (200 ml), and calcium carbonate (50 g) was added in small portions with external cooling (ice bath). The mixture was then filtered, and the material which had been filtered off was washed well with water (200 ml) and methanol (200 ml). The washings were added to the filtrate, evaporated to dryness, and the residue extracted with ethyl acetate (3×100 ml). The extracts were combined, dried (MgSO$_4$), and evaporated to a white solid, 2.73 g. This material was absorbed onto 7 g of silica gel by dissolution in the minimum quantity of a chloroform: methanol mixture (5:1, v/v), addition of the silica gel, and evaporation of the solvents. This silica gel was added as a suspension in ether to a silica gel column (25 g) and eluted with ether containing an increasing proportion of ethanol (2→10%). A proportion of the least polar amide diastereoisomer was eluted first in a pure state, and was recrystallized from ethyl acetate to give colorless crystals of one isomer of the title compound, m.p. 223°-225° C., 105 mg.

Analysis %:
Found: C, 52.8; H, 5.3; N, 18.7.
$C_{13}H_{15}ClN_4O_2$ requires: C, 53.0; H, 5.1; N, 19.0.

The remainder of the product was eluted as a mixture containing both the diastereoisomer characterized above and its more polar diastereomer (1:4 by NMR). Recrystallization from ethyl acetate gave colorless crystals, m.p. 186°-189° C., 404 mg.

Analysis %:
Found: C, 53.0; H, 5.1; N, 19.4.
$C_{13}H_{15}ClN_4O_2$ requires: C, 53.0; H, 5.1; N, 19.0.

EXAMPLE 40

2-(2,4-Dichlorophenyl)-3-(N-methyl-carbamoyl)-1-(1H-1,2,4-triazol-1-yl)butan-2-ol

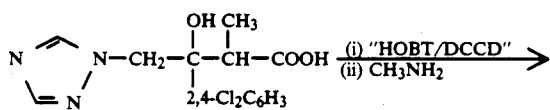

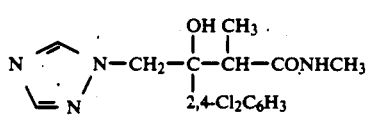

3-Carboxy-2-(2,4-dichlorophenyl)-1-(1H-1,2,4-triazol-1-yl)butan-2-ol (330 mg) was added to dry dioxan (10 ml) followed by 1-hydroxybenzotriazole hydrate ("HOBT") (203 mg) and dicyclohexylcarbodiimide ("DCCD") (618 mg). After stirring for 1 hour at room temperature (20° C.), methylamine (278 mg of 33% [by volume] solution in ethanol) was added and stirring was continued overnight (20 hours). The resulting precipitate of dicyclohexylurea was removed by filtration. The filtrate was added to water (50 ml) and solid sodium bicarbonate was added to pH 8.

The mixture was then extracted with ethyl acetate (3×50 ml) and the combined organic extracts were washed with water, dried (MgSO$_4$) and evaporated. The residue was dissolved in a small volume of methylene chloride and chromatographed on a Merck "Kieselgel 60" (Trade Mark) silica flash column in ethyl ether. Elution with ether (100 ml) followed by 15% (by volume) ethanol in ether (300 ml) yielded, by collection of appropriate fractions, the title compound, 29 mg. m.p. 242°-244° C.

Since the recovered dicyclohexylurea contained a further quantity of the title compound, this was dissolved in a small amount of methanol and absorbed onto Merck's "Kieselgel 60" (Trade Mark) silica (3 g), and the resulting slurry was then loaded onto a 10 g flash column of this material in ethyl ether. Elution with 10% (by volume) ethanol in ether, and collection of appropriate fractions followed by recrystallization from isopropanol, yielded a further quantity of the title compound (81 mg).

Analysis %:
Found: C, 48.9; H, 4.8; N, 16.2.
Calculated for $C_{14}H_{16}Cl_2N_4O_2$: C, 49.0; H, 4.7; N, 16.3.

EXAMPLE 41

(A)

2-(2,4-Dichlorophenyl)-3-ethoxycarbonyl-3-methyl-1-(1H-1,2,4-triazol-1-yl)butan-2-ol
4-(2,4-dichlorophenyl)-3,3-dimethyl-4-(1H-1,2,4-triazol-1-ylmethyl)beta-propiolactone

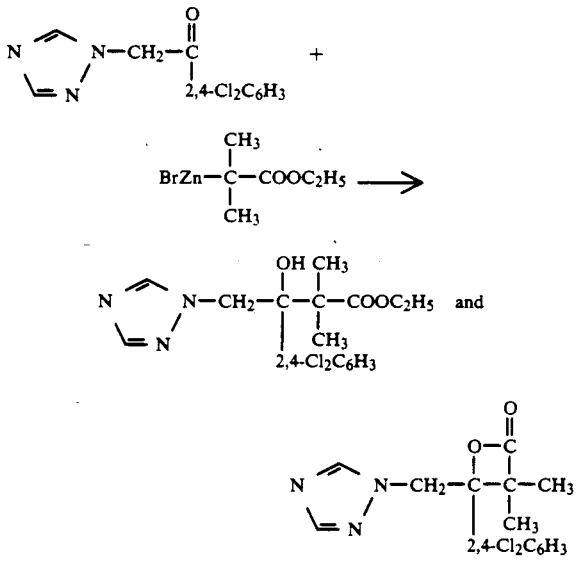

2-(1H-1,2,4-Triazol-1-yl)-2',4'-dichloroacetophenone (2.56 g) in dry tetrahydrofuran (20 ml) and ethyl alpha-bromoisobutyrate (1.475 ml) in dry ether (10 ml) were added simultaneously to granulated zinc (1.5 g) in toluene (10 ml) over 20 minutes. The reaction mixture was then heated at 80° C. for 18 hours. The cooled reaction mixture was poured onto ice-cold sulfuric acid (0.2N, 125 ml) and extracted with ether (200 ml). The ether extract was washed with brine, dried (MgSO$_4$), and concentrated in vacuo. The residue was flash chromatographed on silica (120 g) and eluted with 80% ethyl acetate/20% hexane. The initial fractions yielded the title ester, which was crystallized from ethyl acetate/hexane, yield of the pure product, 61 mg, m.p. 95°–96° C.

Analysis %:
Found: C, 51.7; H, 5.2; N, 11.1.
Calculated for $C_{16}H_{19}Cl_2N_3O_3$: C, 51.6; H, 5.1; N, 11.3.

The later fractions on evaporation gave the title beta-lactone, which was recrystallized from ethyl acetate/hexane, yield of the pure product 240 mg, m.p. 177°–178° C.

Analysis %:
Found: C, 51.8; H, 3.9; N, 12.8.
Calculated for $C_{14}H_{13}Cl_2N_3O_2$: C, 51.5; H, 4.0; N, 12.9.

(B)
3-Carbamoyl-2-(2,4-dichlorophenyl)-3-methyl-1-(1H-1,2,4-triazol-1-yl)-butan-2-ol To a solution of 2-(2,4-dichlorophenyl)-3-ethoxy-carbonyl-3-methyl-1-(1H-1,2,4-triazol-1-yl)butan-2-ol (75 mg) in ethanol (5 ml), aqueous ammonia (sp. gr. 0.88, 12 ml) was added and the solution was left at room temperature (20° C.) for eight days. The solvent was then evaporated in vacuo, the residue was partitioned between methylene chloride and water, and the organic extracts were washed with brine and dried ($MgSO_4$). Removal of solvent followed by flash chromatography on silica (30 g) and elution with a mixture of methylene chloride/methanol/ammonia (93:7:1) gave the title compound, m.p. 162°–163° C. (34.5 mg).

Analysis %:
Found: C, 48.8; H, 4.7; N, 15.8.
Calculated for $C_{14}H_{16}Cl_2N_4O_2$: C, 49.0; H, 4.7; N, 16.3.

C
1-Carbamoyl-2-(2,4-dichlorophenyl)-3-(1H-1,2,4-triazol-1-yl)propan-2-ol was prepared similarly to parts (A) and (B) above from appropriate starting materials, and was confirmed spectroscopically to be identical to the product of Example 4.

(D)
3-Carbamoyl-2-(2,4-dichlorophenyl)-3-methyl-1-(1H-1,2,4-triazol-1-yl)butan-2-ol [alternative method to (B) above]

A solution of 4-(2,4-dichlorophenyl)-3,3-dimethyl-4-(1H-1,2,4-triazol-1-yl-methyl)-beta-propiolactone (70 mg) in ethanol (4 ml) was treated with 0.88 sp. gr. ammonia (6 ml) and left to stand at room temperature for five days. The reaction mixture was then evaporated in vacuo and extracted and chromatographed by the method described in part (B) above to yield the title compound, m.p. 162°–163° C., (41 mg).

Analysis %:
Found: C, 48.6; H, 4.7; N, 15.9.
Calculated for $C_{14}H_{16}Cl_2N_4O_2$: C, 49.0; H, 4.7; N, 16.3.

EXAMPLE 42

2-(2,4-Dichlorophenyl)-3-methyl-3-(N-methyl-carbamoyl)-1-(1H-1,2,4-triazol-1-yl)butan-2-ol A solution of 4-(2,4-dichlorophenyl)-3,3-dimethyl-4-(1H-1,2,4-triazol-1-ylmethyl)-beta-propiolactone (200 mg) in ethanol (5 ml) was treated with a solution of 35% (by volume) methylamine in ethanol (5 ml), and the resulting solution was left to stand overnight at room temperature (20° C.). After evaporating residual methylamine and ethanol, the residue was triturated with hexane and the resulting solid was crystallized from ethyl acetate/hexane to yield the title compound, m.p. 145°–146° C., (120 mg).

Analysis %:
Found: C, 50.2; H, 5.0; N, 15.9.
Calculated for $C_{15}H_{18}Cl_2N_4O_2$: C, 50.4; H, 5.0; N, 15.7.

EXAMPLE 43

(A)
4-(2,4-Dichlorophenyl)-4-(1H-1,2,4-triazol-1-ylmethyl)-beta-propiolactone

3-Carboxy-2-(2,4-dichlorophenyl)-1-(1H-1,2,4triazol-1-yl)propan-2-ol (948 mg) was dissolved in dry dioxan (20 ml) and 1-hydroxybenzotriazole hydrate (0.61 g) followed by dicyclohexylcarbodiimide (1.85 g), was then added. The resulting mixture was stirred at room temperature (20° C.) for two hours, triethylamine (455 mg) was added and stirring was continued overnight (19 hours). The mixture was added to water (100 ml) and extracted with ethyl acetate (3×50 ml). The precipitate of dicyclohexylurea was removed by filtration after the first extraction. The combined organic extracts were washed with water, dried ($MgSO_4$) and evaporated. The residue was dissolved in a small amount of methylene chloride and loaded onto a flash column of Merck's "Kieselgel 60" (Trade Mark) silica (12 g, 230–400 mesh) in ethyl ether. Elution with ethyl ether (100 ml) and then with 5% (by volume) acetone in ether (300 ml) gave, after collection of appropriate fractions, the title compound, 600 mg, m.p. 178°–180° C.

Analysis %:
Found: C, 48.1; H, 3.0; N, 14.0.
Calculated for $C_{12}H_9Cl_2N_3O_2$: C, 48.4; H, 3.0; N, 14.1.

(B)
1-(N-Methylcarbamoyl)-2-(2,4-dichlorophenyl)-3-(1H-1,2,4-triazol-1-yl)propan-2-ol

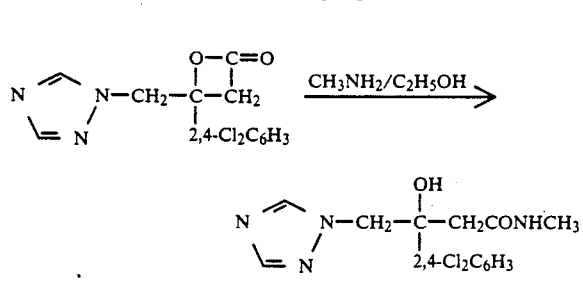

This reaction was carried out by the method of Example 42 using the starting materials specified in the reaction scheme to give the title compound, confirmed spectroscopically to be the desired product and to be identical to the product of Example 5.

EXAMPLE 44

1-Carbamoyl-2-(2,4-dichlorophenyl)-3-(1H-1,2,4-triazol-1-yl)propan-2-ol

This reaction was carried out by the method of Example 41(D) using the beta-propiolactone provided above to give the title compound, confirmed spectroscopically to be the desired product and to be identical to the product of Example 4.

EXAMPLE 45

1-Carbamoyl-2-(2,4-dichlorophenyl)-3-(1H-1,2,4-triazol-1-yl)propan-2-ol

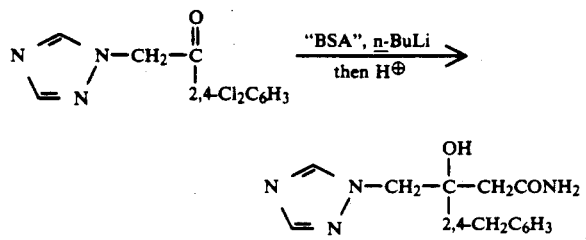

Bis(trimethylsilyl)acetamide (BSA) (1.99 g) was stirred at −70° C. in dry tetrahydrofuran (15 ml) while n-butyllithium in hexane (6.3 ml, 1.55M) was added dropwise over ten minutes. The resulting solution was stirred at −70° C. for 30 minutes, then a solution of 2-(1H-1,2,4-triazol-1-yl)-2',4'-dichloroacetophenone (1.0 g) in dry tetrahydrofuran (10 ml) was added dropwise over 10 minutes, and the mixture was stirred for 1½ hours at −70° C. The reaction mixture was allowed to warm to room temperature, and water (5 ml) and hydrochloric acid (7 ml, 2N) were added. The mixture was adjusted to pH 8 by the addition of solid sodium bicarbonate, and extracted with ethyl acetate (3×10 ml). The combined extracts were washed with saturated sodium chloride solution (3×10 ml), dried (MgSO$_4$), and evaporated to a gum, 1.1 g.

This gum was chromatographed on silica ("Kieselgel 60", Merck), eluting with ether containing 5% by volume ethanol. After the elution of unreacted ketone, the product was eluted. The product-containing fractions were combined and evaporated to give the pure title compound, (0.21 g), confirmed spectroscopically to be identical to the product of Example 4.

EXAMPLE 46

1-Carbamoyl-2-(2,4-dichlorophenyl)-3-(1H-1,2,4-triazol-1-yl)propan-2-ol by acid hydrolysis of nitrile 1-Cyano-2-(2,4-dichlorophenyl)-3-(1H-1,2,4-triazol-1-yl)propan-2-ol (1.0 g) was heated at 60° C. for 2¼ hours in sulfuric acid (10 ml, 80% w/w). The mixture was cooled to room temperature, carefully treated with water (100 ml), and adjusted to pH 9 with solid sodium hydroxide. The resulting solution was extracted with methylene chloride (3×50 ml), and the combined extracts evaporated to a gum, which was chromatographed on silica gel, eluting with methylene chloride containing 3% by volume methanol, increasing to 6% methanol. The fractions which contained the product (as judged by thin-layer chromatography) were combined and evaporated to a white solid, 0.91 g. This was dissolved in a mixture of acetone and methylene chloride at reflux and the product was precipitated by the addition of hexane to give fine crystals, m.p. 144°-145.5° C., 0.61 g, confirmed spectroscopically to be identical with the product of Example 4 after drying under vacuum for 7 hours at 80° C.

EXAMPLE 47

2-(2,4-Dichlorophenyl)-1-[N-(2-[methylsulphinyl]ethyl)carbamoyl]-3-(1H-1,2,4-triazol-1-yl)propan-2-ol 2-(2,4-Dichlorophenyl)-1-[N-(2-[methylthio]ethyl)carbamoyl]-3-(1H-1,2,4-triazol-1-yl)propan-2-ol (0.8 g) and m-chloroperbenzoic acid (85%, 0.35 g, 1 equiv.) were stirred at room temperature in a mixture of isopropanol and methylene chloride (1:1, v/v, 40 ml) for two days. The solvents were then removed under reduced pressure, and the residue was chromatographed on silica (Merck, "Kieselgel 60", 25 g), eluting with a mixture of chloroform, methanol and ammonia (sp. gr. 0.880) (160:20:5, v/v). A portion of the isomer which was eluted first was obtained pure, 116 mg, m.p. 168°-170° C.

Analysis %:

Found: C, 44.1; H, 4.4; N, 13.5.

$C_{15}H_{18}Cl_2N_4O_3S$ requires: C, 44.4; H, 4.5; N, 13.8.

The bulk of the material eluted as a mixture containing both diastereoisomers (330 mg). This material was used in the preparation of the sulphone which follows.

EXAMPLE 48

2-(2,4-Dichlorophenyl)-1-[N-(2-methylsulphonyl]ethyl)carbamoyl]-3-(1H-1,2,4-triazol-1-yl)propan-2-ol The unseparated mixture of diastereoisomers from the previous Example (330 mg) and m-chloroperbenzoic acid (140 mg) were stirred together in a mixture of isopropanol and methylene chloride (1:1, v/v, 20 ml) at 0° C. After one hour at 0° C., the reaction mixture was allowed to reach room temperature and was stirred overnight. The solvents were then removed under reduced pressure, and the residue was dissolved in ethyl acetate (50 ml). The resulting solution was washed with saturated sodium bicarbonate solution (2×20 ml), then with saturated sodium chloride solution (2×20 ml), dried (MgSO$_4$), and evaporated to a gum which was triturated with diisopropyl ether to give a white solid, 209 mg, m.p. 123°-124° C.

Analysis %:

Found: C, 42.6; H, 4.3; N, 13.2.

$C_{15}H_{18}Cl_2N_4O_4S$ requires: C, 42.8; H, 4.3; N, 13.3.

EXAMPLE 49

1-Aziridinylcarbonyl-2-(2,4-dichlorophenyl)-3-(1H-1,2,4-triazol-1-yl)propan-2-ol

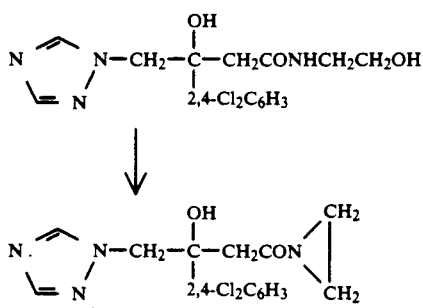

1(N-[2-Hydroxyethyl]carbamoyl)-2-(2,4-dichlorophenyl)-3-(1H-1,2,4-triazol-1-yl)propan-2-ol (1.0 g), triphenylphosphine (1.09 g) and diethyl azodicarboxylate (0.72 g) were stirred at room temperature for 20 hours in dry tetrahydrofuran (20 ml). The reaction mixture was then diluted with water (70 ml) and extracted with ethyl acetate (3×5 ml). The combined organic extracts were washed with saturated sodium chloride solution (2×20 ml), dried (MgSO$_4$), and evaporated to a brown gum. This material was chromatographed on Merck "Kieselgel 60" silica, eluting with 5% by volume ethanol in ether increasing to 10% ethanol in ether. The eluted material, which was one compound as judged by thin-layer chromatography, was crystallized from ethyl acetate/n-pentane to give colorless crystals of the title compound, 441 mg, m.p. 151°–153° C.

Analysis %:
Found: C, 49.2; H, 4.0; N, 16.3.
$C_{14}H_{14}Cl_2N_4O_2$ requires: C, 49.3; H, 4.1; N, 16.4.

EXAMPLE 50

2-(2,4-Dichlorophenyl)-1-thiocarbamoyl-3-(1H-1,2,4-triazol-1-yl)propan-2-ol

A mixture of 1-cyano-2-(2.,4-dichlorophenyl)-3-(1H-1,2,4-triazol-1-yl)propan-2-ol (250 mg), 0,0-diethyl dithiophosphoric acid (0.5 ml) and water (0.1 ml) was heated on steam bath for three hours, evaporated under reduced pressure to an oil, and chromatographed on "Merck 60H" Trademark) silica (10 g) eluting with ethyl acetate. The eluted product, after evaporation, was triturated under petroleum ether (b.p. 40°–60° C.) to give the title compound as a yellow solid (143 mg), m.p 158°–159° C.

Analysis %:
Found: C, 43.8; H, 3.6; N, 16.9.
Calculated for $C_{12}H_{12}Cl_2N_4OS$: C, 43.6; H, 3.6; N, 16.9.

EXAMPLE 51

The following illustrate pharmaceutical compositions for the treatment of fungal infections:

(a) Capsule: 71 parts by weight of the compound of Example 1 or 2 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 3 are dissolved in 10 parts of propylene glycol and mixed into 88 parts of a vanishing cream base.

(c) Pessary 2 parts by weight of the compound of Example 5 are suspended in 98 parts of a warm liquified suppository base which is poured into molds and allowed to solidify.

EXAMPLE 52

By employing the appropriate 2-R-substituted-2-(1H-1,2,4-triazol-1-ylmethyl)oxirane in the procedure of Example 1 or the appropriate ketone in the procedure of Example 2 the following nitriles are obtained.

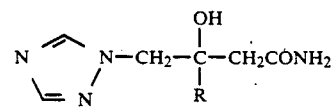

| R | R |
|---|---|
| 4-FC$_6$H$_4$ | 3-FC$_6$H$_4$ |
| 4-ClC$_6$H$_4$ | 3-IC$_6$H$_4$ |
| 4-BrC$_6$H$_4$ | 3-Br-5-IC$_6$H$_3$ |
| 4-IC$_6$H$_4$ | 2-Cl-4-CF$_3$C$_6$H$_3$ |
| 4-CF$_3$C$_6$H$_4$ | 2,4-(CF$_3$)$_2$C$_6$H$_3$ |
| 2-ClC$_6$H$_4$ | 2,4-Br$_2$C$_6$H$_3$ |
| 2-BrC$_6$H$_4$ | 2,5-Cl$_2$C$_6$H$_3$ |
| 2,5-F$_2$C$_6$H$_3$ | 5-chloro-2-pyridyl |
| 2-F-4-ClC$_6$H$_3$ | 4-CH$_3$C$_6$H$_4$ |
| 2-Cl-4-FC$_6$H$_3$ | 4-(CH$_3$)$_2$CHC$_6$H$_4$ |
| 2,4,6-F$_3$C$_6$H$_2$ | 4-(CH$_3$)$_3$CC$_6$H$_4$ |
| 4-Br-2,5-F$_2$C$_6$H$_2$ | 4-n-C$_4$H$_9$C$_6$H$_4$ |
| 2-Cl-4-CH$_3$C$_6$H$_3$ | 2-Cl-4-CH$_3$OC$_6$H$_3$ |
| 4-CH$_3$OC$_6$H$_4$ | 4-n-C$_4$H$_9$OC$_6$H$_4$ |
| 4-Cl-2-CH$_3$O—C$_6$H$_3$ | 2-Cl-4-n-C$_3$H$_7$OC$_6$H$_3$ |

EXAMPLE 53

The nitriles provided in the previous Example are converted to imido ether hydrochlorides by the method described in Preparation A and this intermediate is converted to an amide of the formula below by the method of Example 4.

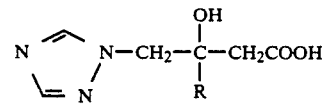

where R is as defined in the previous Example.

EXAMPLE 54

Employing the nitrile provided in Example 3 as starting material in the hydrolysis procedure of Example 6, Part A, provided 1-carboxy-2-(2,4-difluorophenyl)-3-(1H-1,2,4-triazol-1-yl)propan-2-ol, m.p. 185°–187° C.

Analysis %:
Found: C, 50.8; H, 3.9; N, 14.8 4.
Calculated for $C_{12}H_{11}F_2N_3O_3$: C, 50,0; H, 3.9; N, 14.8.

The remaining nitriles provided in Example 52 are converted to the corresponding carboxylic acid of the formula below in like manner.

$$\begin{array}{c} \text{OH} \\ | \\ \text{N} \diagup\!\!\!\diagdown \text{N} - \text{CH}_2 - \text{C} - \text{CH}_2\text{COOH} \\ \diagdown\!\!\!= \text{N} \quad | \\ \quad\quad\quad\quad\quad\quad \text{R} \end{array}$$

EXAMPLE 55

The above carboxylic acids are reacted with the appropriate amine of formula HNR$^2$R$^3$ by the procedure of Example 6, Part B, to provide the amides of the formula below.

$$\begin{array}{c} \text{OH} \\ | \\ \text{N} \diagup\!\!\!\diagdown \text{N} - \text{CH}_2 - \text{C} - \text{CH}_2\text{CONR}^2\text{R}^3 \\ \diagdown\!\!\!= \text{N} \quad | \\ \quad\quad\quad\quad\quad\quad\quad\quad \text{R} \end{array}$$

| R | R$^2$ | R$^3$ |
|---|---|---|
| 4-FC$_6$H$_4$ | H | C$_2$H$_5$ |
| 4-ClC$_6$H$_4$ | CH$_3$ | C$_2$H$_5$ |
| 4-BrC$_6$H$_4$ | H | (CH$_2$)$_5$CH$_3$ |
| 4-IC$_6$H$_4$ | C$_2$H$_5$ | C$_2$H$_5$ |
| 4-CF$_3$C$_6$H$_4$ | (CH$_2$)$_3$CH$_3$ | (CH$_2$)$_3$CH$_3$ |
| 2-ClC$_6$H$_4$ | (CH$_2$)$_3$CH(CH$_3$)$_2$ | (CH$_2$)$_3$CH(CH$_3$)$_2$ |
| 2-BrC$_6$H$_4$ | CH$_3$ | C$_6$H$_5$CH$_2$ |

-continued $$N\underset{N}{\overset{\diagdown}{=}}\hspace{-2pt}\diagup N-CH_2-\underset{R}{\overset{OH}{\underset{|}{C}}}-CH_2CONR^2R^3$$

| | | |
|---|---|---|
| 2,5-F₂C₆H₃ | (CH₂)₃CH₃ | 4-CH₃C₆H₄CH₂ |
| 2-F-4-ClC₆H₃ | H | 4-t-C₄H₉C₆H₄CH₂CH₂ |
| 2-Cl-4-FC₆H₃ | CH₃ | 4-CH₃OC₆H₄CH₂ |
| 2,4,6-F₃C₆H₂ | (CH₂)₅CH₃ | 4-i-C₄H₉OC₆H₄CH₂ |
| 4-Br-2,5-F₂C₆H₂ | CH₃ | 3-ClC₆H₄CH₂CH₂ |
| 2-Cl-4-CH₃C₆H₃ | H | 3-CF₃C₆H₄ |
| 4-CH₃OC₆H₄ | C₂H₅ | 2,4-Br₂C₆H₃ |
| 4-Cl-2-CH₃OC₆H₃ | H | 3,5-I₂C₆H₃CH₂ |
| 3-FC₆H₄ | H | CH₂CF₃ |
| 3-IC₆H₄ | H | 1-adamantyl |
| 3-BrC₆H₄ | H | 2-adamantyl |
| 3-Br-5-IC₆H₃ | C₂H₅ | 2-pyridylmethyl |
| 2-Cl-4-CF₃C₆H₃ | H | 3-pyridylmethyl |
| 2,4(CF₃)₂C₆H₃ | H | cyclopentyl |
| 2,4-Br₂C₆H₃ | H | cyclopropyl |
| 2,4-Cl₂C₆H₃ | CH₃ | cyclohexyl |
| 2,4-Cl₂C₆H₃ | H | cyclobutyl |
| 2,5-Cl₂C₆H₃ | CH₃ | cycloheptyl |
| 5-chloro-2-pyridyl | H | 4-pyridylmethyl |
| 5-chloro-2-pyridyl | CH₃ | CH₃ |
| 5-chloro-2-pyridyl | H | C₂H₅ |
| 5-chloro-2-pyridyl | H | cyclopentyl |
| 5-chloro-2-pyridyl | H | CH₂CONH₂ |
| 4-CH₃C₆H₄ | CH₃ | CH₃CH₂CH=CHCH₂ |
| 4-(CH₃)₂CHC₆H₄ | H | CH₃CH=CHCH₂ |
| 4-(CH₃)₂CC₆H₄ | C₂H₅ | CH₂=CHCH₂ |
| 4-n-C₄H₉C₆H₄ | CH₃ | CH₂CH₂OH |
| 2-Cl-4-CH₃OC₆H₃ | H | (CH₃)₂NCH₂CH₂ |
| 4-n-C₄H₉OC₆H₄ | H | CH₃SCH₂CH₂ |
| 2-Cl-4-n-C₃H₇OC₆H₃ | CH₃ | CH₃SCH₂CH₂ |
| | | ↓ |
| | | O |
| | | ‖ |
| 2,4-Cl₂C₆H₃ | H | CH₃S(O₂)CH₂CH₂ |
| 2,4-Cl₂C₆H₃ | C₂H₅ | C₆H₅OCH₂CH₂ |
| 2,4-Cl₂C₆H₃ | H | 2,4-Cl₂C₆H₃OCH₂CH₂ |
| 2,4-Cl₂C₆H₃ | H | 2,4-F₂C₆H₃OCH₂CH₂ |
| 2,4-Cl₂C₆H₃ | H | 2,4-Cl₂C₆H₃CH₂ |

| R | R²R³ |
|---|---|
| 4-BrC₆H₄ | 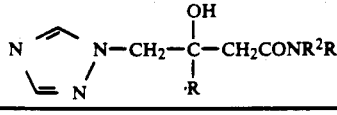 |
| 4-ClC₆H₄ |  |
| 4-IC₆H₄ | 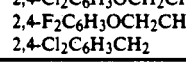 |
| 4-ClC₆H₄ |  |
| 2,4-Cl₂C₆H₃ |  |
| 2,4-F₂C₆H₃ |  |
| 2,4-F₂C₆H₃ |  |
| 2,4-Cl₂C₆H₃ |  |
| 2-ClC₆H₄ |  |
| 4-ClC₆H₄ | |
| 3-FC₆H₄ | |

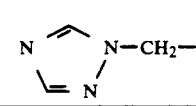

EXAMPLE 56

By employing the appropriate starting carboxylic acid or beta-lactone and amine of formula R²R³NH in place of methylamine in the procedures of Examples 40 and 42, the corresponding amides of the formula below are similarly obtained.

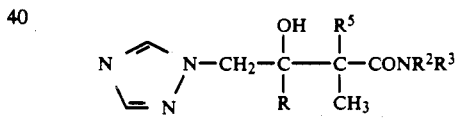

where R⁵ is H or methyl and R, R² and R³ have the values shown in Example 55.

PREPARATION A 3-(2,4-Dichlorophenyl)-3-hydroxy-4-(1H,1,2,4-triazol-1-yl)butyrimidic acid, ethyl ester dihydrochloride 1-Cyano-2-(2,4-dichlorophenyl)-3-(1H-1,2,4-triazol-1-yl)propan-2-ol (1 g) was dissolved in dry ethyl alcohol (100 ml) and dry hydrogen chloride gas was bubbled in, at 0° C., for 10 minutes. The reaction mixture was then stirred at room temperature overnight, and then the solvent was decanted from the solid. The solid was then washed with dry ether and dried to yield the title compound, (1.15 g), m.p. 154°–156° C. The product was used in Example 4.

Analysis %:
Found: C, 40.6; H, 4.4; N, 13.6.
Calculated for C₁₄H₁₆Cl₂N₄O₂.2HCl:
C, 40.4; H, 4.4; N, 13.5.

PREPARATION B (i) 2-(1H-1,2,4-Triazol-1-yl)-2',4'-dichloro acetophenone (Y)

This compound was prepared similarly to the method described in British Patent Specification No. 1,512,918:

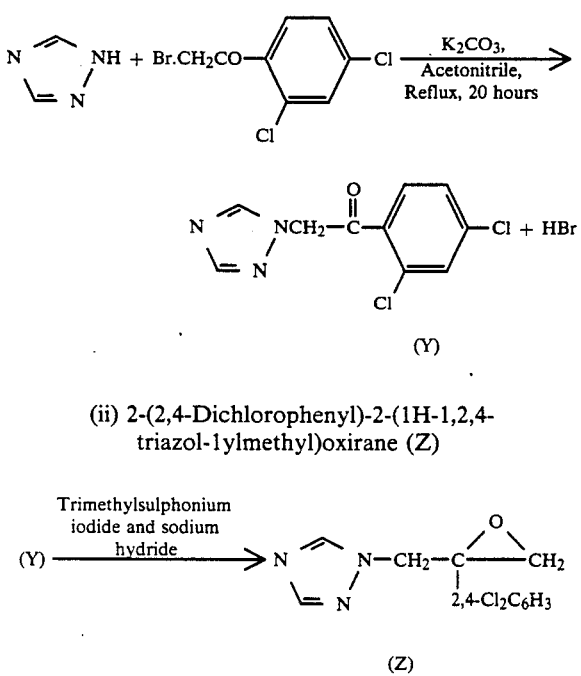

(ii) 2-(2,4-Dichlorophenyl)-2-(1H-1,2,4-triazol-1ylmethyl)oxirane (Z)

In 20 ml of dry ethyl ether, 3.78 g (0.079 mole) of sodium hydride (50% dispersion in oil) was suspended with stirring. The ether was then removed by decantation, and the sodium hydride was dried in a stream of dry nitrogen. Dry dimethyl sulphoxide (100 ml) was added followed by 17.34 g (0.079 mole) of dry powdered trimethylsulphonium iodide, in portions, over 15 minutes. The resulting mixture was stirred for 30 minutes at room temperature (20° C.). 18.33 g (0.072 mole) of compound (Y) as a solution in 50 ml of dry dimethyl sulphoxide was then added. The mixture was heated at 60° C. for three hours and then stood at room temperature overnight. The reaction mixture was cooled and quenched in ice. The product was then extracted with ethyl acetate (600 ml). The ethyl acetate layer was separated, dried over magnesium sulphate, and concentrated to give a red gum. Column chromatography of the gum on silica, eluting with ethyl ether, gave the product (Z). On evaporation, 6.62 g (34.4%) of the title product (Z) was obtained as a gum which solidified on trituration. The pure product melted at 57°–59° C.

Analysis %:
Found: C, 48.6; H, 3.3; N, 15.3.
Calculated for $C_{11}H_9Cl_2N_3O$: C, 49.0; H, 3.4; N, 15.5.

PREPARATION C (i) 2-Chloro-2',4'-difluoroacetophenone

Chloroacetyl chloride (113 g, 1.0 mole) was added dropwise to a stirred mixture of 1,3-difluorobenzene (114 g, 1.0 mole) and anhydrous aluminum chloride (146.6 g, 1.1 mole) at room temperature (20° C.). The mixture was stirred for a further five hours at 50°–55° C. Methylene chloride (48.5 ml) was added slowly as the mixture was allowed to cool to room temperature. The methylene chloride layer was separated, washed with water (2×320 ml) and the solvent removed by distillation at reduced pressure leaving a pale yellow solid (180 g).

A portion of the crude product (145 g) was crystallized from n-hexane (435 ml) giving the title compound (113 g, 73%) m.p. 47°–49° C. (literature* 46.5° C.) IR (KBr) and NMR (CDCl₃) were consistent with the desired structure.

*Von. D. Ehlers, et al., *J. Prakt. Chem.*, 315, 1169 (1973).

(ii)
2',4'-Difluoro-2-(1H-1,2,4-triazol-1-yl)-acetophenone hydrochloride

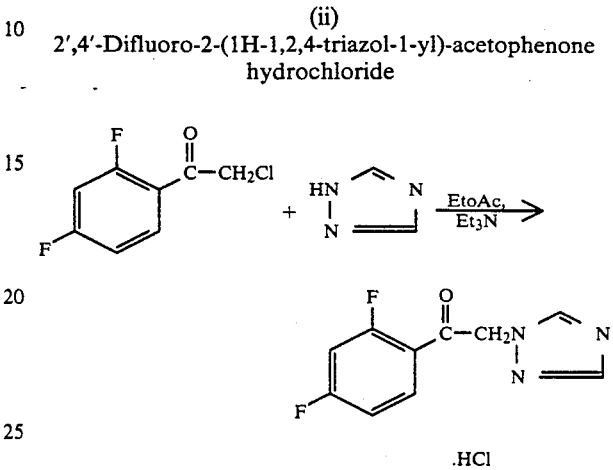

To a mixture of 1,2,4-triazole (30.4 g, 0.44 mole) and triethylamine (15.1 g, 0.15 mole) in refluxing ethyl acetate (186 ml) was added a solution of 2-chloro-2',4'-difluoroacetophenone (38.1 g, 0.2 mole) in ethyl acetate (80 ml). The mixture was refluxed for six hours then cooled to room temperature and the insolubles were removed by filtration. the filtrate was washed with water (2×200 ml) and then the solvent was removed by distillation at reduced pressure. The crude product was dissolved in ethyl acetate (150 ml) then 25% w/v HCl gas in isopropanol was added. The mixture was granulated at 0° C. for one hour and then the solid was collected by filtration and dried to give the title compound (21.6 g, 40%), melting point 167°–170° C. IR (KBr) and NMR (DMSO) were consistent with the desired structure.

This intermediate was characterized as the free base, which was prepared by the following technique:

To a stirred slurry of sodium bicarbonate (16..8 g, 0.2 mole) and 1,2,4-triazole (27.6 g, 0.4 mole) in refluxing toluene (180 ml) was added a solution of 2-chloro-2',4'-difluoroacetophenone (38.1 g, 0.2 mole) in toluene (45 ml). The mixture was stirred at reflux for three hours and the water formed during the reaction was removed using a Dean and Stark trap. The reaction mixture was cooled to room temperature and then water (180 ml) was added. The toluene layer was separated and the solvent removed by distillation at reduced pressure. The resulting pale brown solid was crystallized from 1:1 ethyl acetate:n-hexane (70 ml) giving the title compound (3.9 g), melting point 103°–105° C. The IR (KBr) and NMR (CDCl₃) were consistent with the desired structure.

Analysis %:
Found: C, 53.6; H, 3.15; N, 18.7.
Calculated for $C_{10}H_7F_2N_3O$: C, 53.8; H, 3.2; N, 18.8.

For 4'-chloro-2-(1H-1,2,4-triazol-1-yl)acetophenone see German Patent Application No. 2,431,407.

What is claimed is:
1. A compound of the formula

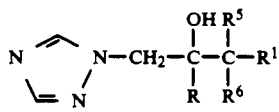 (I)

or a pharmaceutically acceptable acid addition salt thereof,
wherein
R is 2,4-dichlorophenyl, 2,4-difluorophenyl or 4-chlorophenyl;
$R^1$ is —$CONR^2R^3$ where either
(a) $R^2$ is H or $C_1$–$C_4$alkyl, and $R^3$ is H, $C_1$–$C_4$alkyl, —$CH_2CF_3$, carbamoylmethyl, allyl, 2-(methylthio)ethyl, 2-(methylsulfinyl)ethyl, 2-(methylsulfonyl)ethyl, 4-chlorophenylmethyl or 4-chlorophenylethyl; and $R^5$ and $R^6$ are each H or $CH_3$.

2. A compound as claimed in claim 1 wherein R is 2,4-dichlorophenyl or 2,4-difluorophenyl.

3. A compound as claimed in claim 1 wherein $R^1$ is —$CONR^2R^3$ wherein $R^2$ is H, $CH_3$ or $C_2H_5$, and $R^3$ is H, $C_1$–$C_4$ alkyl, 4-chlorophenylmethyl, 4-chlorophenylethyl, —$CH_2CF_3$, carbamoylmethyl, allyl, 2-(methylthio)ethyl, 2-(methylsulfinyl)ethyl, or 2-(methylsulfonyl)ethyl.

4. A compound as claimed in claim 3 of the formula

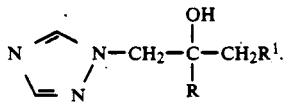

5. A compound as claimed in claim 4 wherein R is 2,4-dichlorophenyl and $R^1$ is $CONR^2R^3$ where $R^2$ is H and $R^3$ is H, $C_1$–$C_3$ alkyl, 4-chlorophenylmethyl, carbamoylmethyl, 2-(methylthio)ethyl, or 2-(methylsulfonyl)ethyl.

6. The compound as claimed in claim 5 wherein $R_1$ is $CONH_2$.

7. The compound as claimed in claim 5 wherein $R^1$ is $CONHCH_3$.

8. The compound as claimed in claim 5 wherein $R^1$ is $CONHC_2H_5$.

9. The compound as claimed in claim 4 wherein R is 2,4-difluorophenyl and $R^1$ is $CONHCH_3$.

10. A compound as claimed in claim 1 of the formula

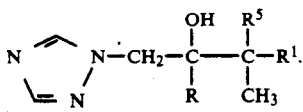

wherein $R^1$ is $CONH_2$ or $CONHCH_3$.

11. A compound as claimed in claim 10 wherein $R^5$ is H and R is 2,4-dichlorophenyl.

12. The compound as claimed in claim 11 wherein $R^1$ is $CONHCH_3$.

13. A compound of the formula

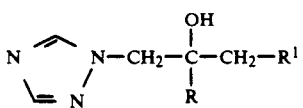

or a pharmaceutically acceptable acid addition salt thereof, wherein R is 2,4-dichlorophenyl and $R^1$ is $CONH_2$, $CON(CH_3)_2$ or $CON(C_2H_5)_2$.

* * * * *